United States Patent [19]

Varnell et al.

[11] Patent Number: 5,142,151
[45] Date of Patent: Aug. 25, 1992

[54] METHOD FOR MEASURING DEGREE OF CURE OF RESIN IN A COMPOSITE MATERIAL AND PROCESS FOR MAKING THE SAME

[75] Inventors: William D. Varnell, Stoddard, Wis.; Mark J. Doty, Ames, Iowa; Scott H. Richgels, La Crescent, Minn.; Trudie M. Knox, Holmen, Wis.; Andrew N. Parfomak, Wallington, N.J.

[73] Assignee: Allied-Signal Inc., Morris Township, Morris County, N.J.

[21] Appl. No.: 598,512

[22] Filed: Oct. 16, 1990

Related U.S. Application Data

[63] Continuation-in-part of Ser. No. 437,945, Nov. 17, 1989, abandoned.

[51] Int. Cl.⁵ ............................................ G01N 21/35
[52] U.S. Cl. ................................... 250/339; 250/343; 374/53
[58] Field of Search ............... 250/339, 340, 341, 343; 374/53

[56] References Cited

U.S. PATENT DOCUMENTS

| | | | |
|---|---|---|---|
| 3,806,730 | 4/1974 | Tirkkonen et al. | 250/341 |
| 4,363,968 | 12/1982 | McGowan et al. | 250/339 |
| 4,372,347 | 2/1983 | Olson | 139/420 |
| 4,414,264 | 11/1983 | Olson | 428/241 |
| 4,577,104 | 3/1986 | Sturm | 250/341 |
| 4,582,520 | 4/1986 | Sturm | 250/339 X |
| 4,609,628 | 9/1986 | Aschenbeck | 436/34 |
| 4,786,817 | 11/1988 | Boissevain et al. | 250/339 |
| 4,798,954 | 1/1989 | Stevenson | 250/341 |
| 4,874,948 | 10/1989 | Cielo et al. | 250/342 |
| 5,019,710 | 5/1991 | Wennerberg et al. | 250/341 |

FOREIGN PATENT DOCUMENTS

WO8401430 9/1982 PCT Int'l Appl. .................... 21/35

OTHER PUBLICATIONS

Patent Abstracts of Japan, vol. 7, No. 117, (P-198)(1262) 21 May 1983, & JP-A, 58-37543 Transform Techniques in Chemistry.

Primary Examiner—Constantine Hannaher
Assistant Examiner—Edward J. Glick
Attorney, Agent, or Firm—Andrew N. Parfomak; Jay P. Friedenson

[57] ABSTRACT

A method for measuring the degree of cure of a resin in a composite material such as a prepreg. The method employs an infrared spectrometer device determining frequency absorbance information of selective frequencies which are representative of the degree of cure of the resin comprised within the prepreg. The method is adaptable for use in on-line production processes for the production of such composite materials.

26 Claims, 14 Drawing Sheets

METHOD FOR MEASURING DEGREE OF CURE OF RESIN IN A COMPOSITE MATERIAL AND PROCESS FOR MAKING THE SAME

REFERENCE TO RELATED APPLICATIONS

This application is a continuation-in-part application of currently copending U.S. patent application Ser. No. 07/437,945 filed Nov. 17, 1989, now abandoned.

TECHNICAL FIELD

The present invention relates to processes for producing composite materials; more particularly the present invention relates to processes for producing composite materials, particularly those comprising a polymer resin which includes process steps directed to determining the amount of cured resin in a composite material which comprises a polymer resin.

BACKGROUND OF THE INVENTION

Composite materials comprising a reinforcement matrix which is coated or in the alternative impregnated with a polymer resin are well known to the art. In many instances, it is desirable to partially cure the polymer resin of the composite material subsequent to the coating or impregnation step in order to form a "prepreg" which possesses desirable rheological properties for easy handling during subsequent processing, for example in formation of a final laminated or structural form. Examples of such materials include those described in U.S. Pat. Nos. 4,414,264, 4,372,347 as well as others.

In the process of producing such composite materials containing a polymer resin, a web formed from fibers, fabric, paper, canvas, or the like of glass, quartz, graphite and/or aromatic polyamide as well as of cellulostic materials in a flexible or fiber form is contacted with one or more polymer resins so to coated and/or impregnate the web which is then subjected to a curing operation wherein at least part of the polymer resin is partially cured. This web impregnated with a polymer resin which has been partially cured and/or dried is commonly referred to in the art as a "prepreg" and this term will be interchageably used to also mean the composite material irregardless of the level of cure of the resin material. Afterwards, the web containing the partially cured polymer resin, or prepreg, may be cut into pieces, layered in register to form a structure which comprises a plurality of layers, and then subjected to further processing wherein the structure is laminated and further curing of the polymer resin is achieved. In many instances, one or more of the layers of the prepreg is imparted with a thin layer of an electrically conducting structure, for example copper, invar copper, aluminum, silver, gold in a foil form prior to, during, or after the ultimate lamination of the layers in order to form a circuit board as is widely used in electronic and/or electrical devices.

An important requirement of the fabrication process of any laminate structure formed from prepregs is the determination of the amount, or degree of cure of the polymer resin, and methods for determining this information have been developed and are known to the art.

Several test methods are known in the art for determining the degree of cure of a resin contained in a composite material. For example, one commonly employed method for determining the degree of cure of a prepreg resin comprises the so called "gel time test", alternately known as the "dry rubber test" or the "tack test". This method involves removing resin from the prepreg and measuring the time required for gelation of the resin to occur at an elevated temperature. Various instruments are used to measure the gelation point. In the electrical laminating industry, this method is performed in accordance with IPC (Institute of Printed Circuits) Test Method No. 2.3.18, which employs a hot platen at 171 deg. C. Other gel tests involve powdering the resin from the composite material and then stirring the powder resin on a hot plate until gelation occurs. One such procedure is that described in U.S. Military Specification MILP-13949 Revision H. These gel time tests are disadvantageous in that they require off-line testing of the composite material and the additional, and often difficult step of separating resin from the composite material. Gel time tests are also disadvantageous in that they are subjective with regard to operator technique and consequent suffer variation in the determination of the gelation point. Further variations which may manifest themselves are due to variations in the platen temperature, as well as variance in the characteristics of the air flow over the sample which affects the rate of cure. Generally, gel tests require from one to two minutes to remove and collect resin from the prepreg or the composite material, and three to ten minutes to measure the gel point and prepare the equipment for the next test. When testing resins having a low degree of cure, an even greater time is required to measure the gelation point.

Another method for determining the degree of cure of a resin in a composite material such as a prepreg is the flow testing method. This method involves measuring the amount of resin which flows out of a fixed number of plies of a prepreg during lamination in a small press. In the electronics industry, this method is generally performed in accordance with IPC Test Method No. 2.3.17 wherein a number of measured samples are cut from the prepreg product, weighed and placed between release forms in a hydraulic press. The samples are pressed at an elevated temperature for ten minutes and them removed from the press. After cooling, a known area is cut from the samples and weighed. The percent flow, which is an indication of the degree of cure, is calculated from the difference in weight per area between the original samples and the pressed samples. The flow testing method is disadvantageous in that it requires at least ten minutes during the pressing portion, and subsequent to pressing requires approximately ten additional minutes for analytical evaluation of the sample. The prepreg product which is tested is destroyed, and the results are determinative of the resin content of the prepreg. This method is also disadvantageous in that operator error can easily occur in one or more of the several handling steps. Such variations and errors my be inconsistencies in the press temperature, the deniations from even distribution of pressure across the surface of the platens, i.e., their "trueness".

A further test which is known for measuring the degree of cure in a composite material is the rheology test method. This method involves measuring the change in viscosity over time of the prepreg resin during cure at elevated temperatures. As in the gel time test, resin must be separated from the prepreg before testing. Once separated, a resin sample is placed in or on an instrument which can measure the change in viscosity over time by measuring the increase in stress during shear of the sample as it cures. This method is based on the property that resins with higher degrees of cure have higher viscosity. Generally, the instrument employed comprises a cone and plate viscometer or parallel plate viscometer, both of which are commercially available. While this test method produces very accurate results, it is disadvantageous in that it requires ten to twenty minutes per sample test and the choice of the shear rate and test temperature can significantly influence the results of the test and its reproducibility.

One technique described in U.S. Pat. No. 4,874,948 to Cielo describes a method and an apparatus which utilizes a laser light source for heating a portion of a polymeric composite material, means for monitoring the temperature fluctuations of the heated surface portion and processing means for utilizing data obtained from the monitoring means for comparing the data with a calibration reference and subsequently providing a measure of the degree of cure of the polymeric composite. This method however materially alters the sample being tested, and while effective in providing a measure of the degree of cure of the surface of a sample does not provide a measure of the degree of cure of the total cross-section of a sample.

A further U.S. Pat. No. 4,582,520 to Sturm describes a system for evaluating the degree of cure of a carbonaceous material web which is used for controlling the operation of an apparatus for producing a fiberglass web used as an insulation material, wherein the system utilizes an infrared radiation apparatus having a plurality of filters wherein limited frequencies may be examined and evaluated.

U.S. Pat. No. 4,798,954 to Stevenson describes a system for monitoring the degree of cure of a resin in a molding press or other molding device.

Several other analytical techniques have also been developed to measure the state or degree of cure of a material including thermal analysis, mechanical analysis, differential scanning calorimetry and dielectric analysis. However, these methods also suffer from one or more of the disadvantages of the method discussed above. For example, both the thermal and dielectric analysis method require significant amounts of time and result in the destruction of the prepreg materials which are tested.

Still further, these methods of analysis generally require physical testing of the polymer prepreg which at least requires that any tested polymer prepreg be removed from a production process, and tested. The analytical methods known to the art are inadequate for use in a production process whereby the degree of cure of the polymer being produced might be utilized in controlling production in that they are (a) time consuming, and (b) frequently require the destruction of at least part of the prepreg being produced.

Accordingly, there exists a continuing need in the art for new and improved methods for the determination of the degree of cure of a polymer resin containing prepreg which is non-destructive and faster than many known methods. A further need is for new and improved methods for the production of composite materials which comprise a polymer resin which is at least partially cured during the production process.

SUMMARY OF THE INVENTION

It is therefore an object of the present invention to provide improved methods for measuring the degree of cure of a resin in a composite material such as a prepreg. The degree of cure may be provided in units which are well known to the art.

It is an additional object of the invention to provide such improved methods which are non-destructive to the composite material and which may be performed in a relatively short period of time.

It is a further object of the invention to provide such improved methods which are independent of operator interaction and which are independent of the resin content in the composite material.

It is a further object of the invention is to provide methods for measuring the degree of cure of a resin in a composite material which are adaptable to on-line testing in the manufacture of the composite material.

A yet further object of the invention is to provide methods for measuring the degree of cure of a resin in a composite material and providing information indicative of the degree of cure.

A still further object of the invention is to provide an improved process for the production of a composite material utilizing a method of testing which is suitable for on-line production wherein the improved process is non-destructive.

A yet further object of the invention is to provide an improved process for the production of a polymer resin containing polymer material wherein the polymer resin is subjected to at least partial curing during the production process.

Finally, it is an object of the present invention to provide such methods which are based on the direct measurement of the chemistry involved during the cure reaction.

These and additional objects are attained by the methods according to the present invention.

More particularly, one aspect of the invention relates to methods for measuring the degree of cure of a resin in a composite material such as a prepreg, which methods employ an infrared spectrometer device having means for resolving specific frequency absorbance information and means for providing a quantitative spectral analysis of the amount of energy absorbed at first and second frequencies of radiation. The first and second frequencies of radiation are characteristic of unreactive and cure-reactive groups, respectively, contained in the resin. The method of the present invention comprises irradiation the composite material with the infrared light source, generating a quantitative spectral analysis of the amount of energy absorbed at the first and second frequencies, determining the height of or area under the spectral curve centered about a spectrum maximum at each of the first and second frequencies, and calculating the ratio of one of the determined height or area values to the at least one other of the determined height or area values to provide a measurement of the degree of cure of the resin. The calculated ratio is independent of the resin content of the composite material and may be compared with a predetermined calibration between such calculated ratios and with measurements derived from one or more of the methods presently employed in the art, for example the gel time test methods. The methods according to the present invention allow non-destructive testing of the prepreg material in a relatively short period of time.

In another aspect of the invention there is provided an improved process for the production of composite materials containing at least one polymer resin, wherein the process includes on-line methods and means for determining the degree of cure of the polymer resin effected during the production process and further includes means for controlling process variables responsive to the means for determining the degree of polymer cure for controlling the production of the polymer composite.

These and additional objects and advantages provided by the methods of the present invention will be more fully apparent in view of the following detailed description of the invention.

BRIEF DESCRIPTION OF THE DRAWINGS

The following detailed description will be more fully understood in view of the accompanying drawings of which a brief description follows.

DETAILED DESCRIPTION OF THE INVENTION

Figure 1:
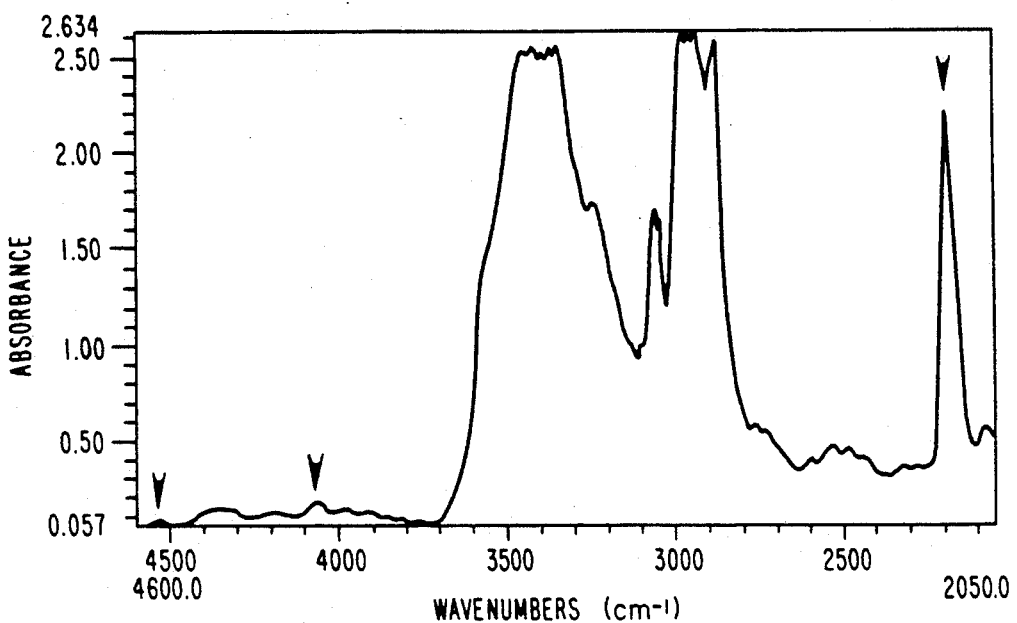
FIG. 1 represents a spectral analysis generated in accordance with the present method as described in Example 1.

The composite materials of the present invention generally comprise a web of a reinforcement matrix which is coated and/or impregnated with a resin. Non-limiting examples of such materials include those described in U.S. Pat. Nos. 4,414,264, 4,372,347 as well as others patents not particularly enumerated here. As has been stated, such composite materials are commonly referred to as "prepregs." Commonly employed reinforcement matrix materials comprise fibers, fabric, paper, or the like formed of glass, quartz, graphite and/or aromatic polyamides such as KEVLAR, a high molecular weight polyolefin fiber as well as from cellulostic fibers. The web may be coated and/or impregnated with one or more polymer resins known in the art. Resins suitable for use with the present invention may be any resin which is capable of being utilized in a laminate structure and which may be cured by thermosetting. Such resins are numerous and well known to the art, and frequently feature one or more of the following desirable characteristics: a relatively low coefficient of thermal expansion, good dimensional stability, low dielectric constant, solvent resistance, low moisture absorption and the like.

The methods of the present invention employ an infrared spectrometer device having means for resolving specific frequency absorbance information and means for providing a quantitative spectral analysis of the amount of energy absorbed at a first frequency and at least a second frequency of radiation, which frequencies are characteristic of unreactive groups which are constituted in resin, and of cure-reactive groups which are constituted in the resin used in forming the composite material. That is, the first frequency is characteristic of an unreactive group contained in the composite material resin which does not undergo chemical reaction during the curing reaction, while the second frequency is characteristic of a reactive group contained in the composite material which undergoes a chemical reaction during the curing reaction.

The reactive group may be any group comprised in the polymer resin which undergoes a chemical reaction during the curing process. By way of example and not by limitation, the reactive group may be reactive groups selected from among: epoxy, nitrile, alkenyl, maleimide, acetyl, acid, cyanate, phenol, styrenic, hydroxyl, and amine groups. Of these, the preferred reactive groups are epoxy, nitrile, cyanate, phenol and maleimide, and the most preferred is an epoxy group. Other groups not particularly listed here but exhibiting the desired behavior may also be utilized.

The non-reactive group may be any group contained in the resin which does not undergo a chemical reaction during the curing process, and which will not evaporate, burn off, or in any other way be lost during the curing process. This non-reactive group may be any such group comprised within the resin composition. These reactive groups are commonly found in the backbone portion of typical polymers and may include aromatic rings, C-H, and C-R groups, where "R" is representative of an alkane.

Figure 4:
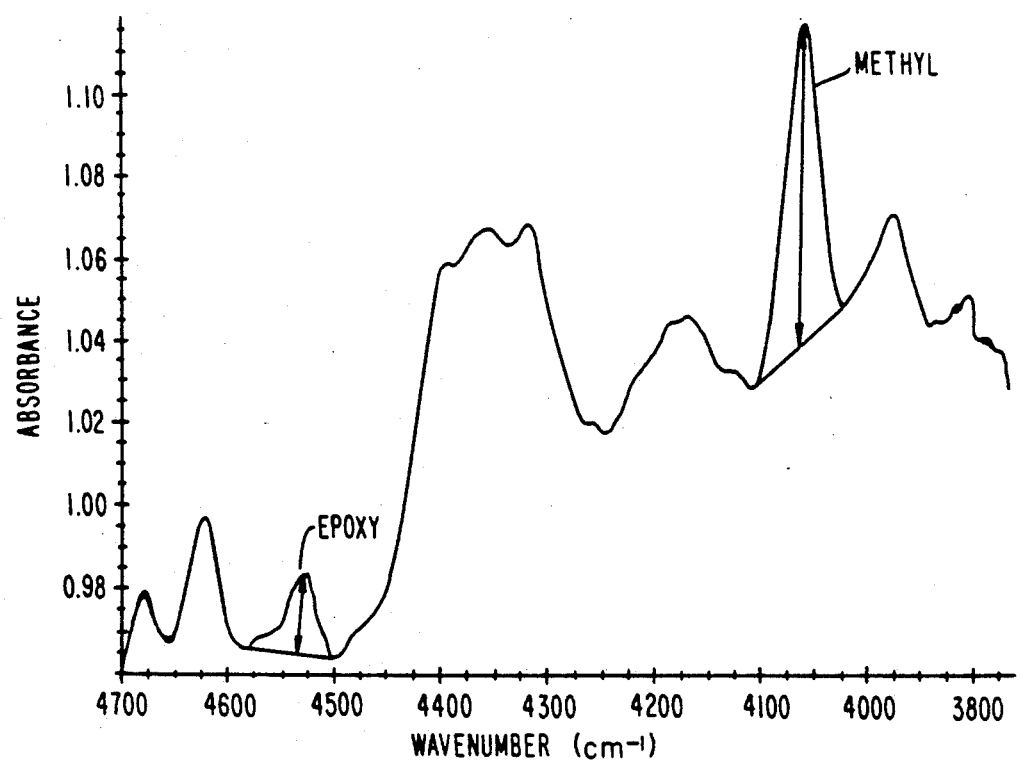
FIGS. 4 to 6 represent spectral analyses generated according to the present method as described in Example 2.
Figure 5:
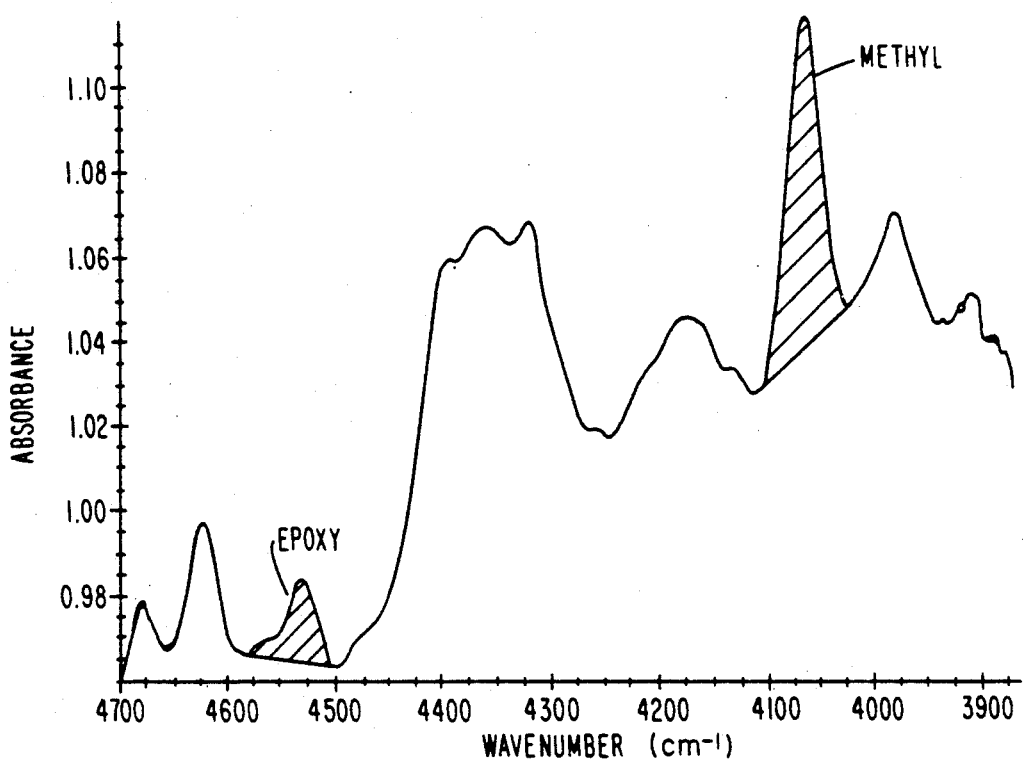
Figure 6:
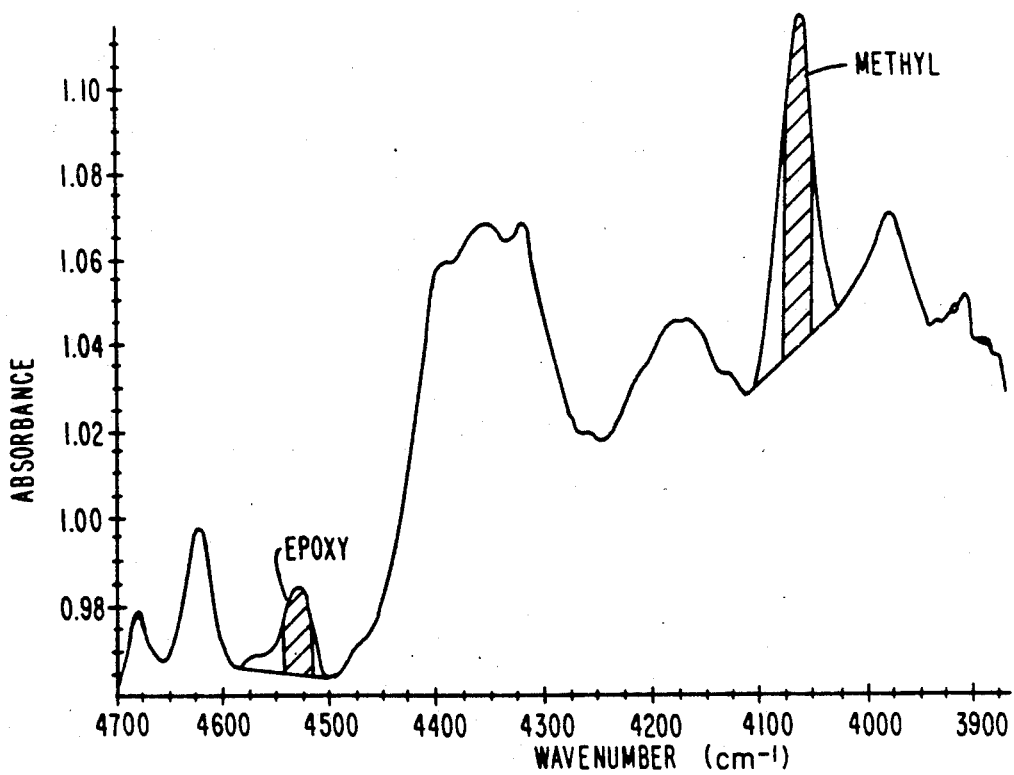

The first frequency and the at least second frequency of radiation which are characteristic of the non-reactive and reactive groups, respectively, are preferably selected to be present in the IR spectrum outside of the range of the absorptive range of the materials comprising the web so that the resulting IR spectra can be distinctly determined without the influence of the absorptivity of the web. What is to be understood by "frequency" in discussions directed to the first and second frequencies is that the frequency is the maximum of a band of frequencies which may be expressed in any conventional units including wavenumbers. The "frequency" is meant to describe the position on the spectral curve centered about the spectral maximum, and it is this frequency which is used in subsequent evaluative procedures. By way of illustration, alternative evaluations of the "height" or "area" are possible; these methods are known to the art and several of these are illustrated in FIG. 4, 5 and 6 which are discussed below.

A preferred infrared spectrometer device for use in the present invention comprises a Fourier transform infrared spectrometer, or "FTIR". Fourier transform infrared spectrometers are commercially available from various sources. Several commercial models presently available are employed in the examples set forth below. Typically these FTIR devices include a source of infrared light, such as a halogen lamp or bulb, a sensor means for detecting light transmitted through a material being evaluated, and processing means for processing signals received from the sensor means and providing signals representative of the infrared spectrum received by the sensor means. Of these spectrometers those which are operative in the range outside the absorbance range of the web, such as glass fiber or olefinic fiber, is generally to be preferred. For comprising glass fiber webs, this preferred range corresponds approximately to 2000 $cm^{-1}$ to 7000 $cm^{-1}$ which is a range within which the characteristic frequencies of the selected reactive and non-reactive groups are found to occur in the IR spectra, and which reactive groups are in frequencies which fall outside of the absorptive range of the web, as has already been discussed.

It is known to the art that infrared devices comprise three types: those which utilize a moving filter wheel, those which include gratings interspersed intermediate a light source and the material being examined in order to generate the frequency distribution, and those which utilize a single light source for providing the light over a wider range of frequencies with which the sample is examined. While FTIR devices are of this this category, infrared devices of the first and second categories may enjoy the benefit of the instant invention as well, although those of the third type which function without the intermediate grated filter wheel are generally to be preferred. This is in part due to the nature of these types of apparati and their method of operation; those utilizing a grating may exhibit "drifting" or deviation from the particular frequency being evaluated, by as much as 10 $cm^{-1}$ from the actual frequency which is desirably to be examined. Those using a filter are specific to a particular frequency; examination of a range of frequencies requires changing multiple filters. Such effects decrease the accuracy of the determination of the IR spectrum of a sample being examined, particularly the characteristic peaks indicative of the radiation absorbed due to the prior reaction of the reactive groups, preferably epoxide groups, during the curing step of a production process and consequently reduces the accuracy of the overall process for determining the degree of cure of a composite material. Preferably an FTIR is used as such devices exhibit minimal "drifting" characteristics, and further have a faster sampling rate as all frequencies are simultaneously measured in a single sampling operation. Such is not possible with the other types of infrared devices. These FTIR type devices while not completely free from "drifting" or other deviation, typically exhibit an amount of drifting an order of magnitude less than that of those of the grating or filter wheel type ranges. This reduced "drift" is normally between about 0 and 1 $cm^{-1}$. With such a reduced level of "drifting" the accuracy of the measurement derived is improved and consequent determinations of the relative degree of cure are more accurate. A further feature is that FTIR type devices suffer little or no appreciable deviation in their calibrations over longer periods of time, i.e. one month or more, and especially six months or more. As such, their accuracy and repeatability of their calibrations and of their consistent operation is assured. The importance of this consideration and the accuracy of the method of the present invention should be apparent as the method of the present invention is strongly dependent upon the determination of two or more frequencies within the broad IR spectra which is received by the FTIR and subsequently subjected to evaluation by the processor means.

The present methods comprise irradiating the composite material with the infrared light source of the infrared spectrometer device and generating a quantitative spectral analysis of the amount of energy absorbed at first and second frequencies. The spectral analysis of the amount of energy absorbed at the first frequency acts as a reference in order to determine the amount of resin contained in the composite material subjected to measurement. On the other hand, the spectral analysis of the amount of energy absorbed at the second frequency is a measure of the degree of cure reaction which has taken place in the composite material, as well as providing a further indication of the amount of resin contained in the composite being sampled. These first and second frequencies must each be in a region of the infrared spectra where other absorbance bands do not overlap with overlap the absorbencies of interest, or the absorbance band of the material used in constructing the web.

Once the quantitative spectral analysis has been generated, the amounts of energy absorbed at the first and second frequencies are compared. More specifically, this involves determining the height of the spectrum maximum at each of the first and second frequencies, and calculating a ratio of one of the two determined values to the other so to provide a measurement of the degree of cure of the resin. Methods for determining the height and/or area under a spectrum maximum at a frequency are known to the art, and are described in *Transform Techniques in Chemistry*, Peter R. Griffiths, Editor, particularly in Chapter 11 entitled "Fourier Domain Processing of General Data Arrays" pps. 285–305, especially at the sub-section titled "Differentiation and Integration" starting at pg. 299, and in Chapter 4 "Data Handling in Fourier Transform Spectroscopy", pp. 69–108, as well as in other references known to the art. The ratio may be calculated as the determined value at the first frequency with respect to the determined value at the second frequency or as the value at the second frequency with respect to the value at the first frequency. The calculated ratio is a direct measure of the extent of the chemical reaction which occurs during curing of the prepreg resin. These calculated ratios may be correlated with other prepreg test results to create a predetermined calibration relationship which maybe be used for product evaluation.

An important feature of the invention is that the calculated ratio is based on the spectral analysis of the first frequency of radiation which is characteristic of unreactive groups contained in the resin, which is compared with a spectral analysis of the second frequency of radiation which is characteristic of reactive groups contained in the resin. That is, the unreactive group reference peak is used to normalize the reactive group peak, thereby eliminating the effect of the resin content, i.e., the quantity of resin in a tested sample of composite material. Thus, the calculated ratio which is a measure of the degree of cure of the resin is also independent of the amount of resin contained in the composite material. Without this internal reference, accurate measurement of the weight of the resin in the composite material would be required before the degree or extent of cure could be determined. The unreactive reference peak can also be used as a measure of the resin content, i.e. the amount or resin contained in the composite material or prepreg, since its area is a measure of the amount of the resin in the prepreg.

Since the prepreg undergoes no further curing during testing according to the present methods, repeated cure measurements are possible. Additionally, the present measuring methods are non-destructive. The present methods may be effected either on-line in the prepreg manufacturing process or off-line. For on-line measurements, the prepreg may be moved between the infrared light source and the detector of the infrared spectrometer device. For example, the infrared light may be directed from the spectrometer using mirrors or optical fibers to the prepreg and, in a similar manner the infrared light, once passed through the composite material sample, may be returned to the spectrometer for analysis. In off-line measuring, small pieces of prepreg may be provided for spectrometer testing, as well as pieces which are meant to be final products for subsequent use, as in a manufacturing or assembling process or product of a subsequent user, and thereby conserves saleable product. The present methods are independent of operator interaction and allow measurements to be computed in a relatively short period of time. These advantages of rapid evaluation of degree of cure and operator independence, as well as other advantages, allow for the use of the testing method in a production process for composite materials.

Figure 16:
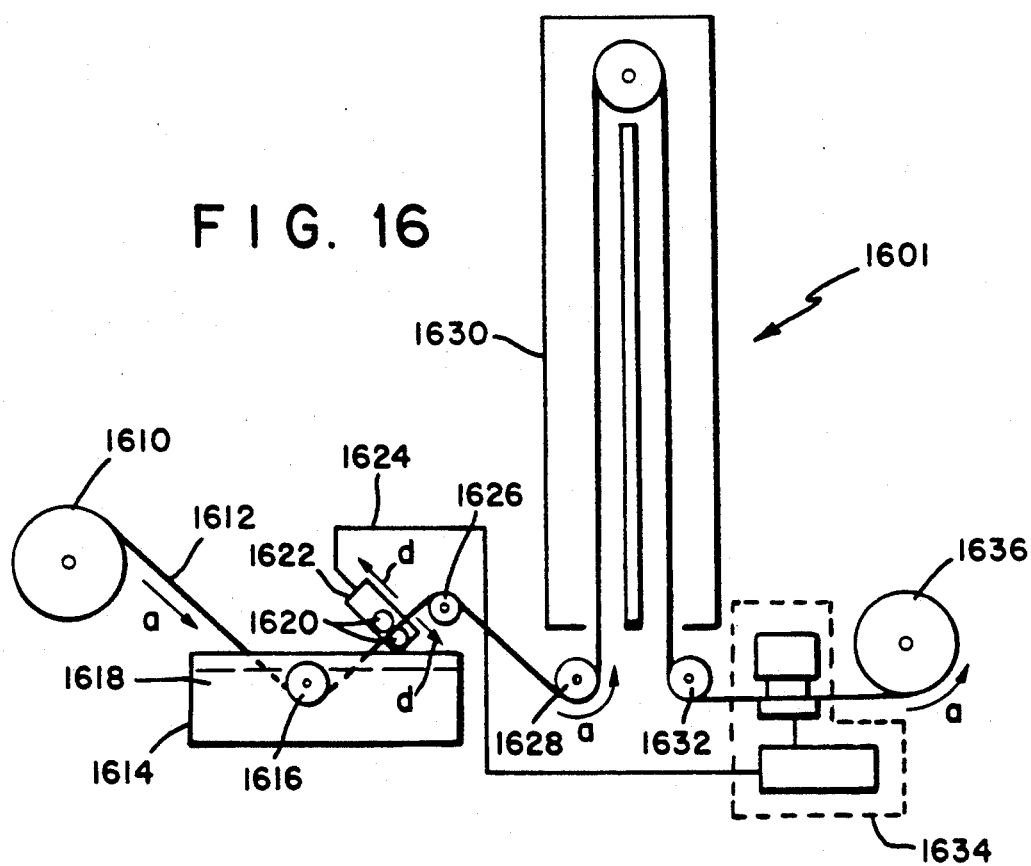
FIG. 16 represents a process for producing a prepreg according to the present invention wherein the means for determining the degree of cure are used to control the spacing of metering rollers.

In accordance with the benefits of the present invention, a process for producing a prepreg according to the present invention wherein the means for determining the degree of cure is incorporated into a typical process and is used to control the spacing of metering rollers is illustrated in FIG. 16. Therein, the process apparatus 1601 comprises a source of supply of the unimpregnated web, herein indicated as a supply spool 1610. The web 1612 is taken off the supply spool 1610 and is drawn in the direction of the arrow labeled "a" into a vessel 1614 containing a quantity of the resin used to impregnate the web 1612. Herein is depicted a single embodiment which may be suitably used, which comprises a vessel 1614 and a roller 1616 partially submerged in the resin 1618 and positioned so that web 1612 passing into the vessel 1614 and passing underneath the roller 1616 is submerged in the resin 1618 and is thereby impregnated. The impregnated web 1612 next passes through a nip between a pair of metering rollers 1620 in order to control the amount of resin which is impregnated in the web 1612 by varying the intermediate distance between the roll centers. The metering roller 1620 include means which are responsive to a control signal for varying the position of the position of the metering rollers 1620. This direction is shown by the two arrows labeled "d" which are meant to represent a direction perpendicular to the surface of the web 1612. This intermediate distance between roll centers is maintained by a device 1622 responsive to a control signal received along the control line 1624.

The impregnated web 1612 exiting the metering roller 1620 passes over a subsequent rollers 1626, 1628 before entering the drying/curing oven 1630 wherein partial curing of the resin is effected. The web 1612 exits the drying/curing oven 1630 passes under a further roller 1632 before being subjected to testing in accordance with the instant invention and subsequent collection on a take-up spool 1636. In this figure the apparatus enclosed in dashed lines and labeled 1634 depicts an FTIR communicatively coupled to a data processor which acts to process the signals of the FTIR in accordance with the invention's teachings and to provide a control signal along control line 1624. In a preferred embodiment the control line 1624 carries electrical signals to the device 1622 which maintains the distance between the metering rollers 1620. It should be apparent by reference to this figure that the evaluation of the degree of cure performed by the apparatus 1634 evaluates the web 1612 which now forms a prepreg and is used to provide a control signal to vary a process variable. Herein the distance between the metering rollers 1620 is the process variable which may be varied, as such a variation ultimately effects the final product quality. It should further be apparent that other process instrumentalities other than the nip between metering rollers 1620 may be varied in order to effect the ultimate product quality and as such are considered to be process variables in accordance with the present invention's teachings.

Figure 17:
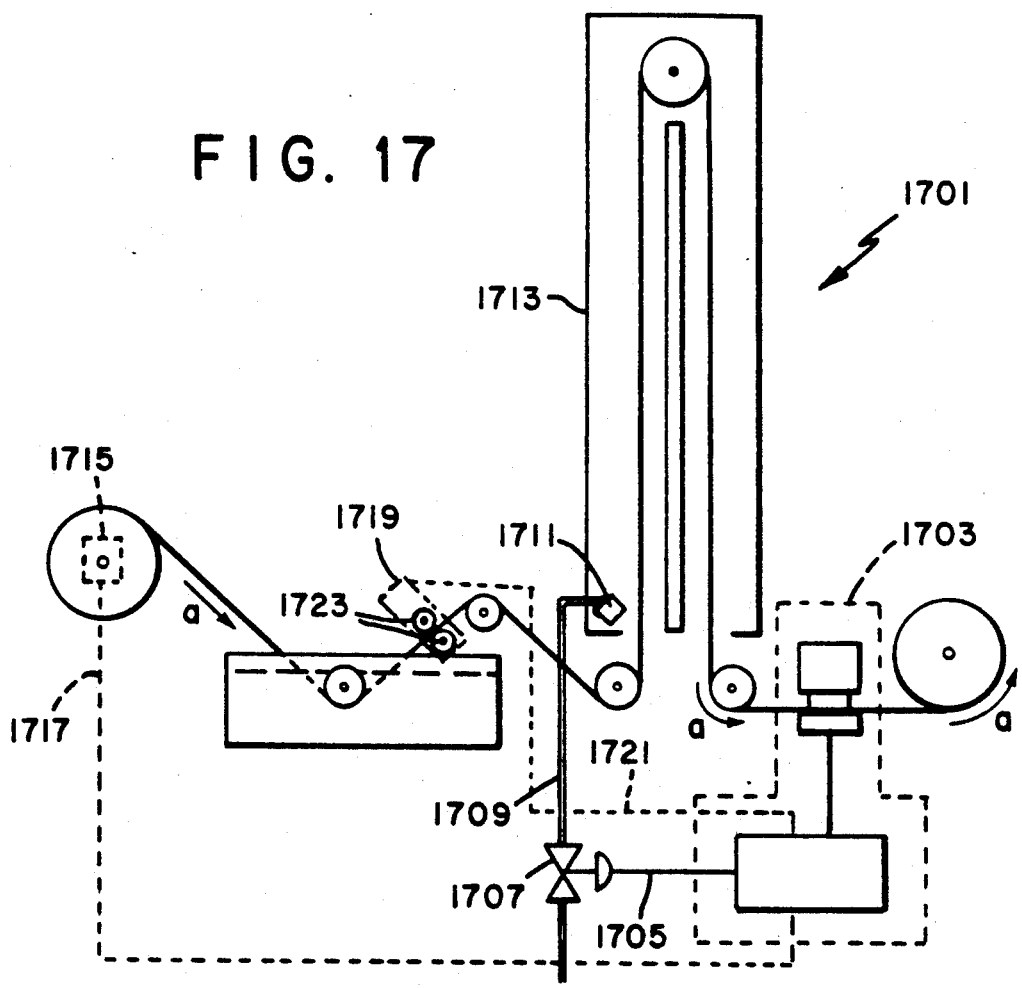
FIG. 17 represents a process for producing a prepreg according to the present invention wherein the means for determining the degree of cure are used to control the heating means of a resin cure oven.

An alternative process to that of FIG. 16 is depicted on FIG. 17. Therein is depicted a similar process apparatus 1701 and an apparatus enclosed in dashed lines and labeled 1703 depicting an FTIR communicatively coupled to a data processor which acts to process the signals of the FTIR in accordance with the invention's teachings. In this embodiment, the apparatus 1703 provides signals along a signal line 1705 to a valve 1707 which meters the supply of gas flowing through a supply line 1709 to a burner 1711 within the drying/curing oven 1713. The rate of gas supply is a direct control over the mode of heating of the drying/curing oven and is a further process variable affecting the final product quality. Also shown in phantom view is thereon a speed controller 1715 which is responsive to signals received over a signal conductor 1717 and which is used to vary the rate of the feed of the web in the process, and thereby control the throughput rate of the process. Further shown in phantom view is a controller 1719 responsive to signals received over signal conductor 1721 for controlling the nip width of metering rollers 1723 which illustrates the control of a further process variable. Thus with regard to the various features illustrated on FIG. 17, it should be apparent to the skilled practitioner that a plurality of process variables may be controlled in the production process of the instant invention.

Figure 18:
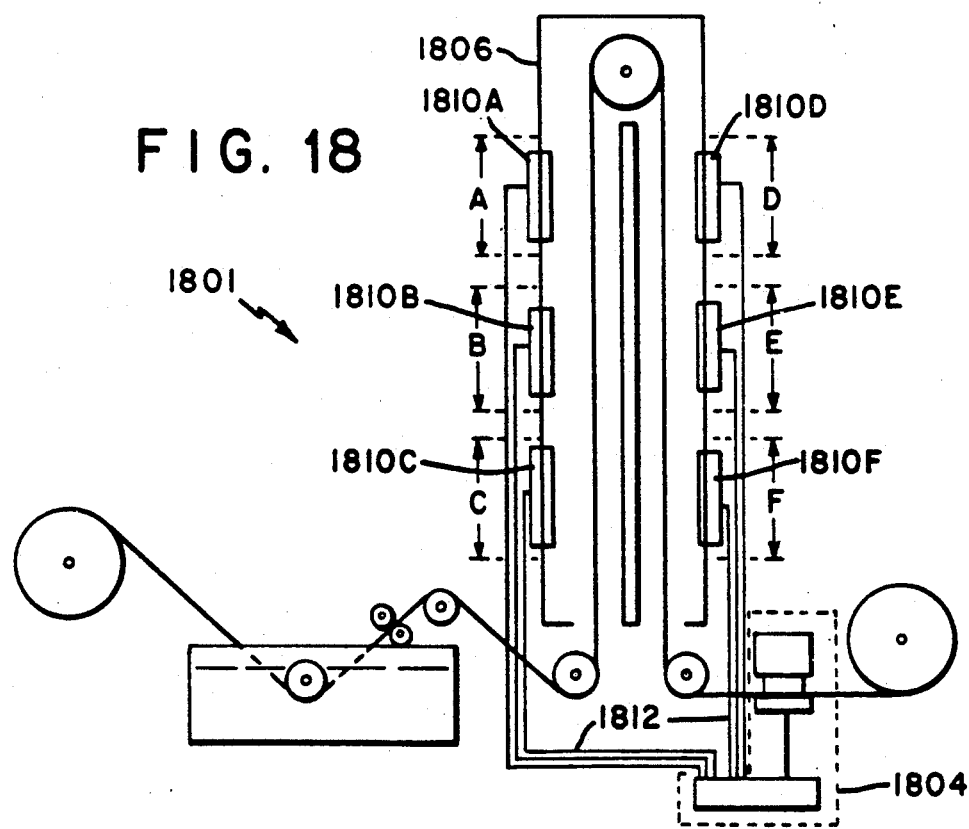
FIG. 18 represents a process for producing a prepreg according to the present invention wherein the means for determining the degree of cure are used to control multiple electrical resistance coils used in the resin cure oven having multiple heating/curing zones.

In a further embodiment of the invention shown in FIG. 18, a process apparatus generally designated 1801 includes an apparatus enclosed in dashed lines and labeled 1804 depicting an FTIR communicatively coupled to a data processor which acts to process the signals of the FTIR in accordance with the invention's teachings. The process apparatus 1801 further comprises a drying/curing oven 1806 with a plurality of heat sources 1810A-1810F which generally define a plurality of heating zones labeled A-F. The individual heat sources 1801A-1801F receive control signals from the apparatus 1804 which provides appropriate control signals via signal conductors 1812, and thereby varies the mode of heating of the drying/curing oven. The advantage of a drying/curing oven 1806 with a plurality of heating zones is in the feasibility of more precise control over the drying/curing operation of an impregnated web and improved product quality.

Figure 19:
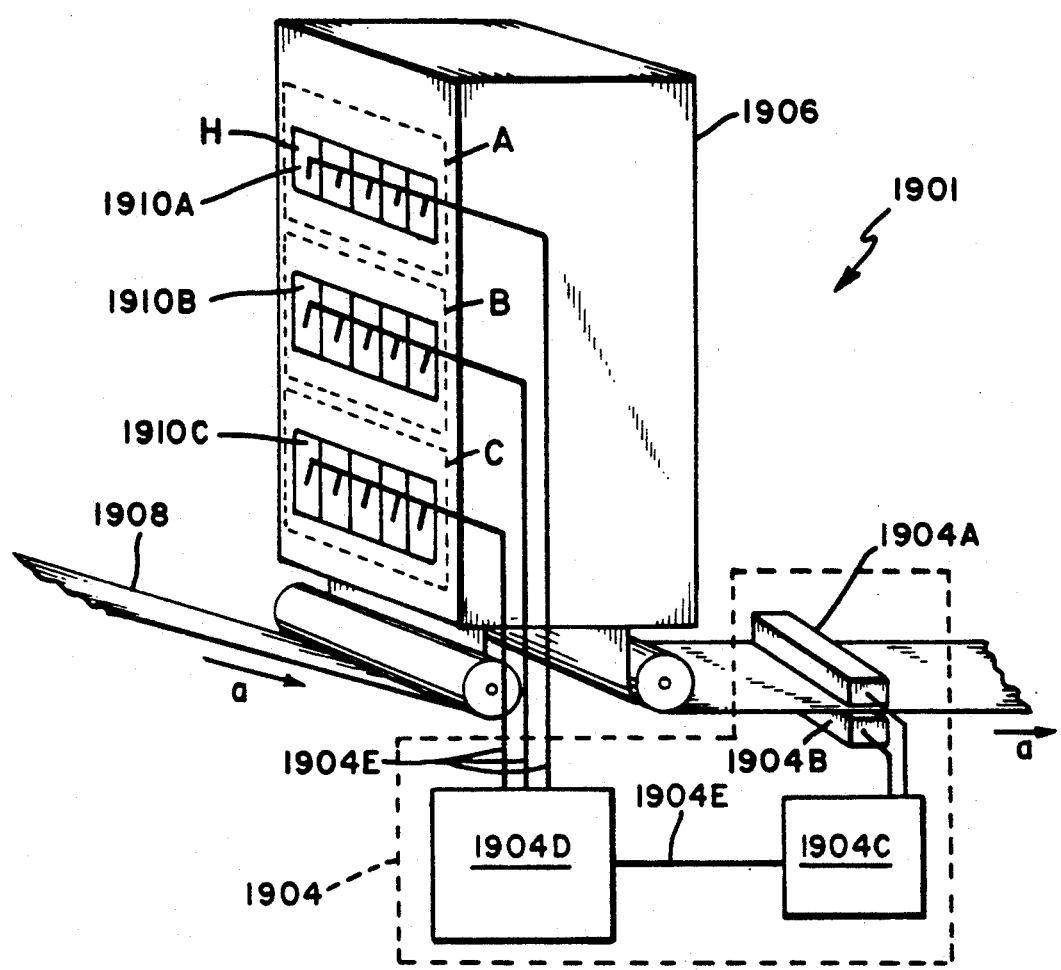
FIG. 19 is a perspective view of a portion of a process similar to that depicted in FIG. 18.

FIG. 19 is a perspective view of a portion of a process designated 1901 and illustrates an apparatus enclosed in dashed lines and labeled 1904 depicting an FTIR communicatively coupled to a data processor which acts to process the signals of the FTIR in accordance with the invention's teachings, and a drying/curing oven 1906. The elements of the apparatus 1904 include an infrared light source element 1904A on one side of a web 1908, a corresponding receiver 1904B on the other side of the web, both the light source element 1904A and the receiver 1904B communicatively connected to an apparatus comprising the FTIR device 1904C, and a controller 1904D responsive to signals received from the device 1904C via a signal transmission means 1904E and for providing suitable control signals over signal transmission means 1904E. As may be seen from the Figure, the signal transmission means 1904E are communicatively connected to a plurality of heating elements arranged in rows labeled 1910A, 1910B and 1910C which within heating zones generally defined by the dotted lines labeled A, B, and C. Each of the rows of heating elements arranged in rows labeled 1910A, 1910B and 1910C are comprised of a plurality of heating elements, one of which is labeled "H", arranged in the drying/curing oven 1906 so to be in a direction transverse to the web 1908 passing therethrough. In a preferred embodiment and meant to be designated here, the heating elements arranged in rows are of the electrical resistance type and are responsive to signals received over the signal transmission means 1904E from the controller 1904D of the apparatus 1904. The elements of the apparatus 1904 include an infrared light source element 1904A on one side of a web 1908 which has a plurality of light sources, a corresponding receiver 1904B on the other side of the web which has a plurality of receiving elements adapted to correspond to the plurality of light sources. In this manner, multiple determinations of the degree of cure of the web 1908 may be determined for regions in the transverse direction of the web 1908, and in accordance with the teachings of the invention, analyzed. In turn, responsive to the degree of cure determined, an appropriate signal may be transmitted to one or more of the heating elements in one or more of the rows labeled 1910A, 1910B and 1910C in order to vary the heat being supplied to the web in the oven, so to correct any deficiencies in the web 1908 being produced.

Figure 20:
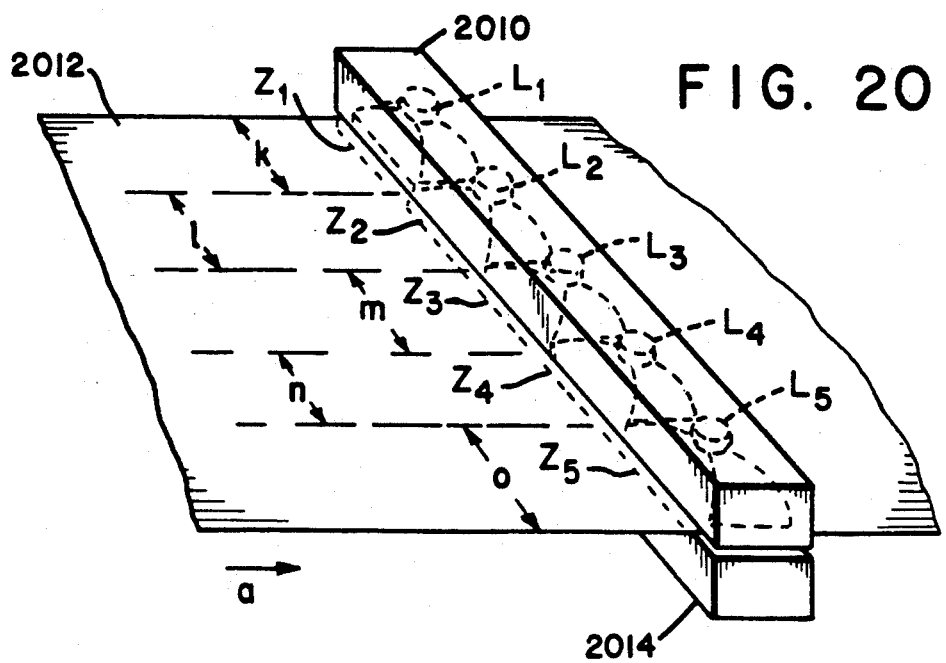
FIG. 20 is a view of a portion of a process including a prepreg and an embodiment of a FTIR which includes a plurality of IR light sources and a plurality of corresponding IR light receivers.

FIG. 20 is a view of a portion of a process including a web and an embodiment of an FTIR apparatus which includes a plurality of IR light sources and a plurality of corresponding IR light receivers. A unit 2010 includes a plurality, particularly five halogen lamps labeled L1-L5 and shown in phantom which act as IR light sources which, when operating impinge upon the web 2012 in individual zones labeled $z_1$-$z_5$. These zones correspond to a strip of the prepreg material being produced. A plurality of appropriate receivers of the transmitted IR light corresponding to each of the individual zones labeled $z_1$-$z_5$ but not illustrated in the Figure are enclosed within a second unit 2014 and are arranged so that an appropriate receiver receives light from only one of the lamps L1-L5. In such an arrangement, the light passing through a particular portion of the web 2012 may be used to determine the degree of resin cure of that portion of the web 2012 as each of the lamps L1-L5 impinges only on a limited zone $z_1$-$z_5$ which corresponds generally to a longitudinal portion of the web, representatively labeled by a letter in the series k through o. With such an FTIR which includes a plurality of IR light sources and a plurality of corresponding IR light receivers a variety of alternative embodiments may be realized.

Incorporating such an FTIR into the process described in conjunction with FIG. 19, the degree of cure of a portion of a web 2012 may be determined by means of lamp L1 which shines on the web 2012 in zone $z_1$; the IR light transmitted therethrough is in turn received by an appropriate receiver which is then analyzed in accordance with the teachings of the present invention. Accordingly, an appropriate control signal may then be transmitted to a particular heating element, such as "H" representing a heating element which is so positioned relative to the web so to generally correspond with the relative position of the lamp L1 and its appropriate receiver relative to the web. In such manner, the collected light received for a particular position of the web may be used to subseuently determine an ultimate control signal used to control a process variable. In an alternative embodiment, the light received by a plurality of the receivers corresponding to a plurality of the lamps L1-L5 may be combined and averaged to ultimately provide a measure of the average degree of resin cure across the transverse direction of the web. Yet further, a plurality of the lamps L1-L5 may be used to provide particularized evaluation of the degree of resin cure in only selected zones of a web.

Figure 21:
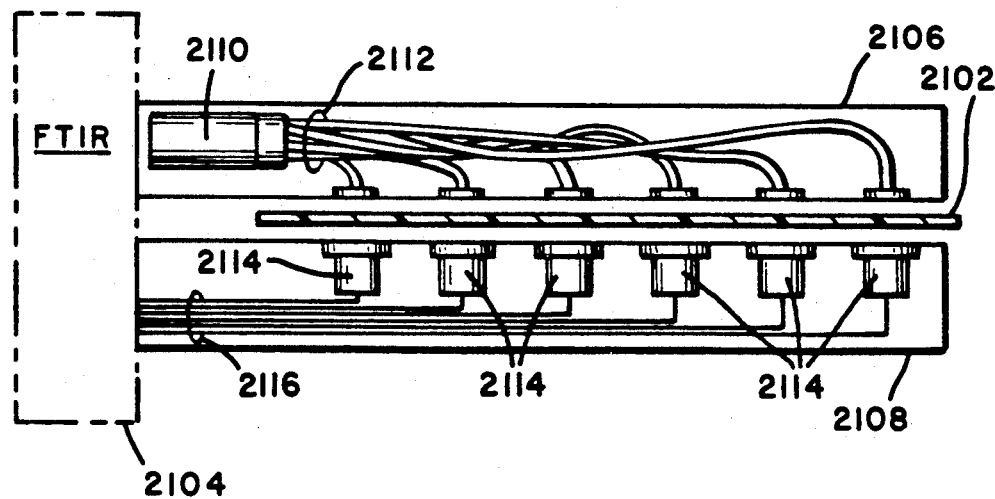
FIG. 21 is a side view of an embodiment of a portion of the FTIR having a plurality of waveguides.

FIG. 21 is a side view of an embodiment of a portion of the FTIR having a plurality of waveguides. Therein, the prepreg 2102 (which is shown only in a cross-sectional view) is at least partially positioned between a first housing 2106 and a second housing 2108 which are part of the FTIR 2104, a portion of which is shown in phantom. Although FIG. 21 depicts the housings 2106, 2108 as being adjacent to the FTIR 2106 as being either affixed thereto or forming a part thereof, it is to be understood that the remainder of the FTIR 2104 may form a distinct further and separate unit. A suitable light source 2110 provides radiation in the suitable frequency range via a series of waveguides 2112 which are so directed so to direct the radiation onto one side of the prepreg in a plurality of positions. Any material which may act as a waveguide within the frequency range of use may be incorporated, however optical fibers are mentioned as preferred embodiments. The second housing 2108 includes a plurality of receivers 2114 which are correspondingly positioned with the positions of the waveguides 2112 so that transmitted radiation from the waveguides 2112 passing through the prepreg 2102 will be received by a respective receiver 2114. Signals from the receivers pass over signal conductors 2116 to the balance of the FTIR apparatus 2104 for further processing in accordance with the present invention's teachings.

Figure 22A:
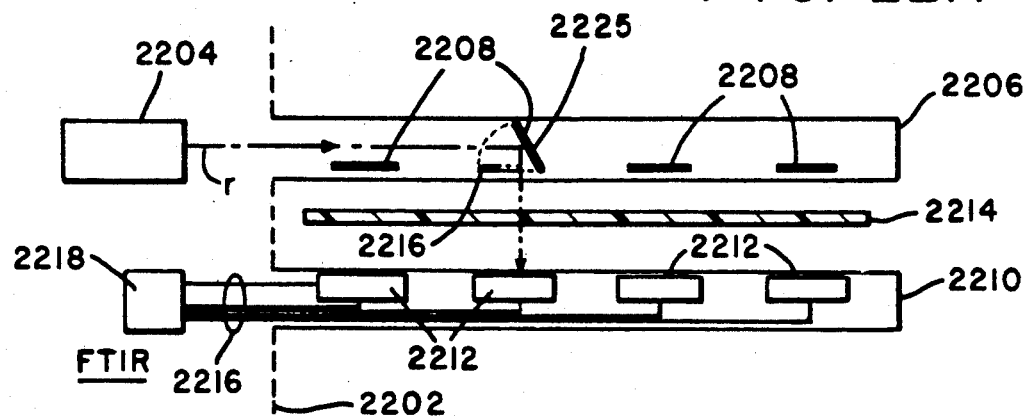
FIG. 22A is a side view of an alternate embodiment of a portion of the FTIR.

FIG. 22A is a side view of an alternate embodiment of a portion of the FTIR which may be used with the present invention which depicts a portion of an FTIR 2202 which includes a light source 2204 capable of providing the radiation in the range of frequencies suited for use, a first housing 2206 containing a plurality of moveable mirrors 2208, a second housing 2210 containing a plurality of receivers 2212 for receiving the radiation transmitted through the composite material 2214 which is positioned therebetween and which is shown in FIG. 22 in a cross-sectional view. The receivers 2212 are communicably connected to the FTIR 2202 by means of appropriate signal conductors 2216, here electrical signal conductors connected to further signal processing means 2218 capable of further signal analysis.

Depicted on FIG. 22A is a mirror 2208 which is further indicated as 2225 which is shown to be in an inclined position suited to redirecting a ray of radiation from labelled "r" the light source 2204 through the prepreg composite material 2214 and to a respective and appropriately placed receiver 2212. A drawing of this mirror 2225 in phantom and labelled 2226 represents the mirror in a non-inclined position. This is indicative of the operation of all the mirrors 2208 in this embodiment, more particularly that, in like manner as that shown by mirror 2225, that each mirror 2208 may be moved from a first position, such as indicated by the position labelled 2226 where the mirror 2208 does not redirect the radiation transmitted by the light source 2204 to a second, reflecting position as indicated by 2225 wherein the light is redirected through the composite material 2214. In such an embodiment, each mirror 2208 may be individually moved from a first non-reflecting position to a second reflecting position, and while the radiation, as indicated by a ray labeled "r" is redirected, a signal received by a 2212 of radiation transmitted through the prepreg 2214 may be received, and signals directed via signal conductors 2216 for further processing. In such an embodiment, a single light source may be used with a plurality of receivers, providing an FTIR capable of sampling several areas of the composite material.

Figure 22B:
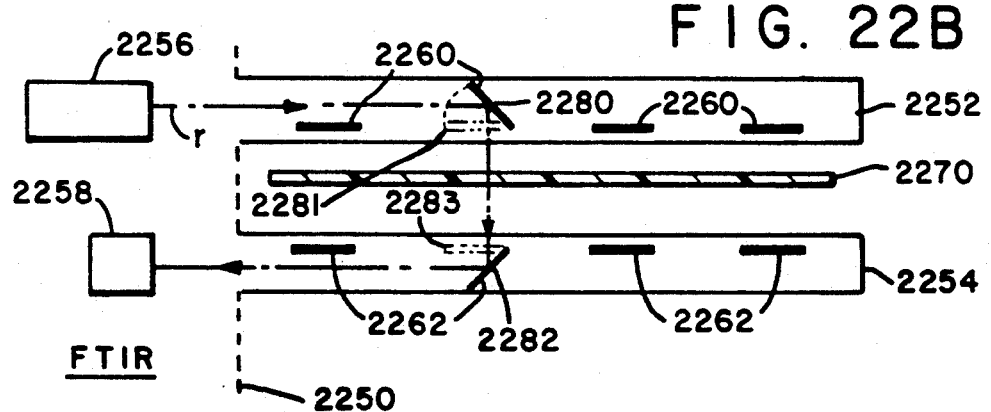
FIG. 22B is a side view of an alternate embodiment of a portion of the FTIR similar to that depicted in FIG. 22A.

The following FIG. 22B is an alternative embodiment of the portion of the FTIR of FIG. 22A. Therein the FTIR 2205 includes a first housing 2252 and a second housing 2254, a radiation source 2256 and a radiation receiver 2258. The first housing 2252 has an internal arrangement of moveable mirrors 2260 which operate in the same manner as the plural mirrors 2208 of FIG. 22A. Further, the second housing 2254 of FIG. 22B further includes a system of complimentary mirrors 2262 which function in the same manner as those of the first housing 2252. In such an arrangement, which forms a preferred apparatus for use in conjunction with of the instant invention, only a single radiation source and a single radiation receiver are needed. By way of example, a light ray labeled "r" exiting the radiation source 2256 is deflected by a mirror additionally labeled 2280 which has been moved from its normal position shown in phantom and labeled 2281 through a portion of the prepreg 2270 where it is redeflected by a second mirror additionally labeled 2282 which has been moved from its normal position which is shown in phantom and additionally labeled 2283 and directed into the single radiation receiver 2258. In such an arrangement, each of the mirrors 2260 in the first housing 2252 functions cooperatively with a mirror 2262 in the second housing 2254 in deflecting radiation through the composite material 2270. By alternating the motion of the mirrors 2260, 2262 the degree of cure of various portions of the prepreg 2270 may be evaluated.

Figure 23:
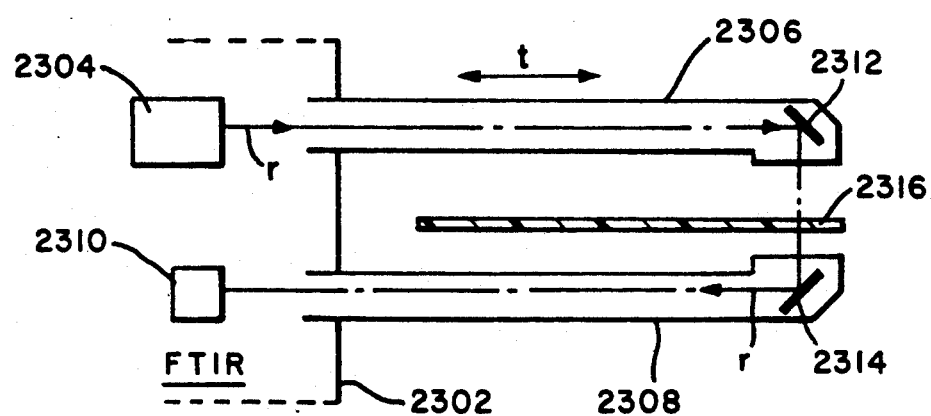
FIG. 23 is a side view of a yet further embodiment of a portion of the FTIR.

FIG. 23 is a side view of a yet further embodiment of a portion of the FTIR 2302 which finds use in the present invention. The FTIR 2302 includes a suitable light source 2304, a first housing 2306, a second housing 2308 and a radiation receiver 2301. The first and second housings 2306, 2308 each contain a mirror 2312 and 2314 capable of redirecting radiation emitted by the light source 2304 as indicated by a ray labelled "r" so that a path from the light source 2304 is redirected so to pass through the composite material 2316 (which is shown in a cross-sectional view) and again redirected to receiver 2310. While the use of mirror 2312, 2314 is not essential to the proper operation of the invention, their use provides a cost effective construction for a suitable FTIR apparatus. A feature of the embodiment is that the first and second housings 2306, 2308 are bidirectionally moveable in the direction of the two-headed arrow "t" of the figure; in this manner various portions of the composite may be sampled by the repositioning of the first and second housings 2306, 2308.

Figure 24:
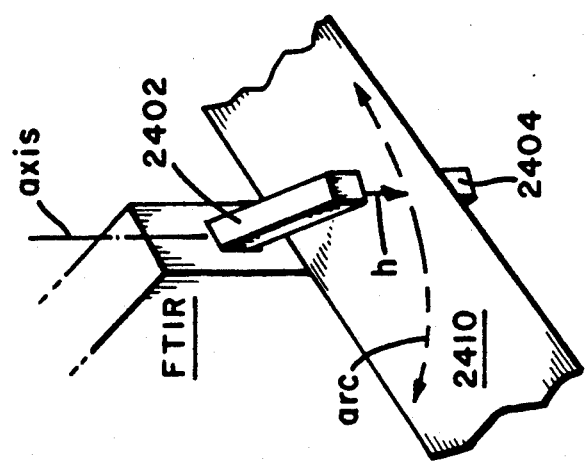
FIG. 24 is a perspective view of a portion of an embodiment of the FTIR.

FIG. 24 is a perspective view of a portion of an embodiment of the FTIR functionally and structurally similar to that described in FIG. 23, with the further feature that the upper and lower housings, 2402, 2404 are pivotally moveable along an axis, here labeled "axis" so to provide that the relative position of the mirrors (not shown here) may be positioned in two axes by allowing the upper and lower housings, 2402, 2404 to simultaneously rotate about the axis and define a non-linear arc labeled "arc". The position of the upper housing 2402 determines the direction of the transmitted radiation (indicated by the ray "h") and directed to the composite material 2410 which is to be collected by an appropriate radiation receiver on the lower housing 2404. In this manner an alternative to the linear type positioning motion of the housings shown on FIG. 23 is provided by the "sweeping" motion of the housings of FIG. 24, as well as an appropriate apparatus for effecting the same.

The processes herein described are by way of illustration, and aspects of each may be combined in any manner, an substitutions of elements may be made without departing from the teachings of the invention. For example, other processes for producing composites having an arrangement different from those described here may be used. Variations of the processes may be made, such varying a plurality of process variables, such as having the apparatus which comprises the FTIR and the controller exhibit control over both metering rollers such as those of FIG. 16 and the gas supply of the drying/curing oven of FIG. 17, or the heating elements of drying/curing ovens of FIGS. 18 and 19. Such processes have already been suggested, and illustrated in FIG. 17, although it is also recognized that further process variables may be utilized. A preferred process variable subject to control is the rate of the supply of the web, or the web speed of the process as the rate of the supply influences the complete process. In further preferred embodiments, the variation of web speed may also be in conjunction with variations in any other process variable, either individually or jointly, including variations in the metering rollers and/or the operating characteristics of the heating/drying oven. Variations in the structure of the apparatus comprising the FTIR and the controller may be made; whereas the Figures have depicted them as separate elements, they may be combined into one element or assembly which provide the same functions.

Further particular embodiments of methods according to the present invention are illustrated in the following examples.

EXAMPLE 1

This example demonstrates a method according to the present invention for measuring the degree of cure of a resin in a composite material. The composite material comprised a prepreg formed of a woven E-glass fabric impregnated with a brominated epoxy resin formulation. The resin formulation comprised 100 parts by weight of a brominated epoxy resin (DOW XU 71881) having a weight per epoxy between 440 and 500 and containing 19 to 21 wt % bromine, 2.6 parts by weight dicyandiamide curing agent, 0.11 parts 2-methylimidazole catalyst and 32 to 50 parts by weight solvents including acetone, dimethylformamide (DMF), and propylene glycol ether. Pieces of the prepreg were cured by exposing the same to heat at 325° F. in a forced air oven for varying periods of time. The resulting prepreg samples were subjected to gel time test in accordance with IPC Test Method 2.3.18 using a hot plate at 171° C. Samples were also subjected to measurement of the degree of cure in accordance with the present method using a Nicolet 5-PC Fourier transform infrared spectrometer. The quantitative spectral analysis set forth in FIG. 1 was generated.

With reference to FIG. 1, the first frequency of radiation characteristic of unreactive groups contained in the resin is centered at 4060 cm$^{-1}$ representative of an unreactive methyl group contained in the resin. A second frequency of radiation characteristic of cure-reactive groups is centered at 4529 cm$^{-1}$, representative of a cure-reactive epoxy group contained in the resin. An additional second frequency of radiation characteristic of cure-reactive groups contained in the resin is centered at 2180 cm$^{-1}$, representative of a cure-reactive nitrile group contained in the resin. The areas below the spectrum maximum of each of these frequencies was determined, after which the ratio of the determined value at the second frequency to the determined value at the first frequency was calculated. The method was repeated on additional prepreg samples heated for varying periods of time.

Figure 2:
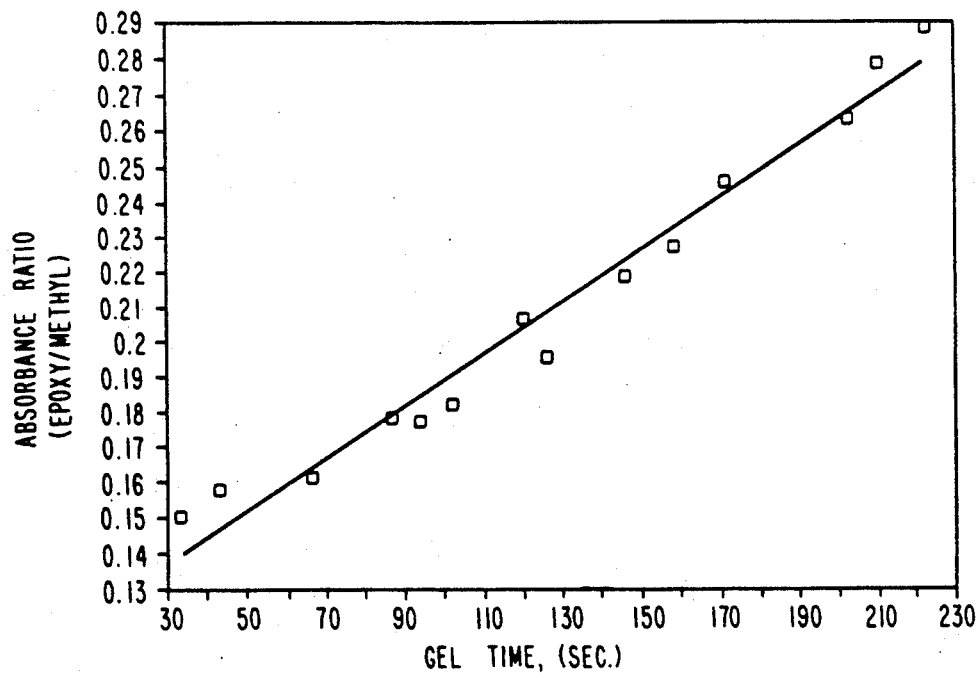
FIGS. 2 and 3 represent calibrations prepared as described in Example 1.
Figure 3:
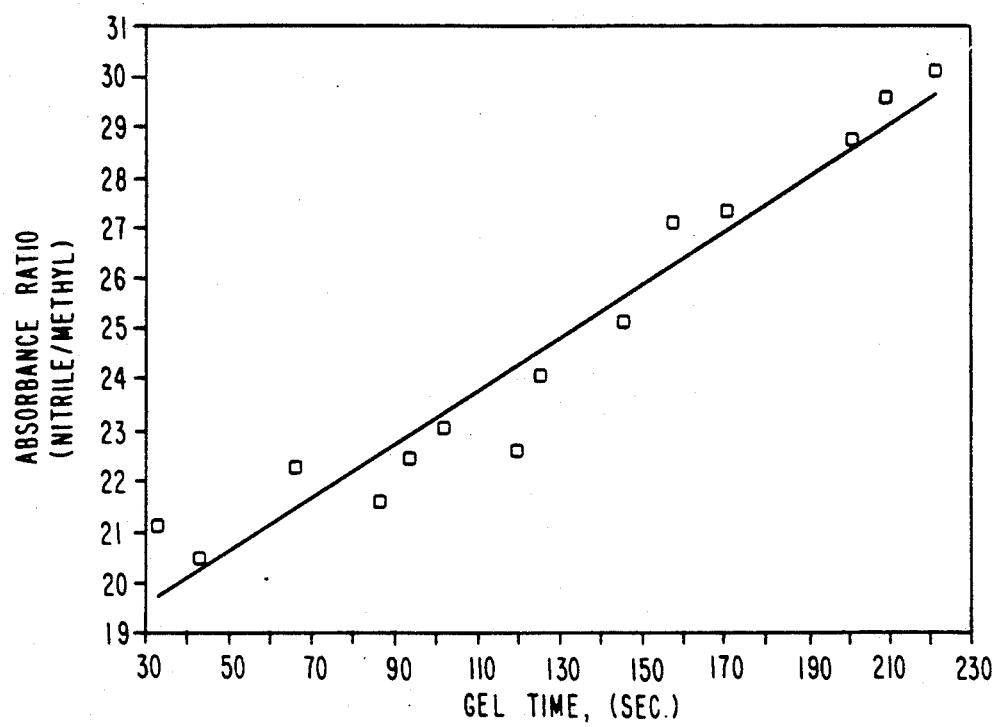

The resulting calculated ratios were then correlated with the results of the gel time test to produce the calibrations set forth in FIG. 2 (nitrile/methyl ratio) and FIG. 3 (epoxy/methyl ratio). As is evident from FIGS. 2 and 3, an excellent correlation between both the epoxy/methyl ratio and the nitrile/methyl ratio and the gel time test results is provided. The measurements made according to the methods of the present invention required approximately one to two minutes per sample to perform while the gel time testing required approximately five to eight minutes per sample, which included the time to prepare the sample and apparatus for the testing process. Once obtained, the correlation between gel times and the calculated ratios can be used to quickly and accurately evaluate the gel time of other prepreg samples prepared from similarly formulated resin systems.

EXAMPLE 2

This example further demonstrates the methods according to the present invention. The composite material employed in this example was similar to that described in Example 1 and comprised a woven fiber glass fabric impregnated with a brominated epoxy resin described in Example 1, 2.6 to 2.9 parts by weight dicyandiamide curing agent, 0.11 parts by weight 2-methylimidazole catalyst or 0.2-0.4 parts by weight benzyl dimethylamine catalyst and 35-45 parts by weight solvents including dimethylformamide, acetone, methyl celosolve and propylene glycol monomethylether. The prepreg was prepared in a production treater in a manner common to the prepreg manufacturing industries. During the prepreg preparation, the solvents were evaporated with heat and the resin was partially cured. A set of samples with various degrees of cures was prepared by changing the temperature and/or the duration time in the prepregging oven and obtaining samples from separate production batches.

Pieces of the prepreg samples were cut and subjected to measurement according to the present method using various infrared spectrometers. FIGS. 4, 5 and 6 set forth the quantitative spectral analyses generated according to the present invention using a Biorad FTS-7 spectrometer, a Nicolet 8205 spectrometer and an Analect FSS 40 spectrometer, respectively. As shown in FIG. 4, the ratio of the reactive epoxy group absorbance to the unreactive methyl group absorbance was determined from measurement of the height of the spectrum maximum at each of the indicated frequencies. As shown in FIG. 5, the ratio was determined from measurement of the entire area under the absorbance peaks at the frequencies of interest while as shown in FIGS. 6 the ratio was determined by measuring the area of a central slice of each of the absorbance peaks at the frequencies of interest. Additionally, each of the instruments employed in this example included instrument software which was programmed to automatically calculate the desired ratio. Each instrument performed the measuring method according to the invention; from time of sample loading to completed calculation, less than one minute passed.

Figure 7:
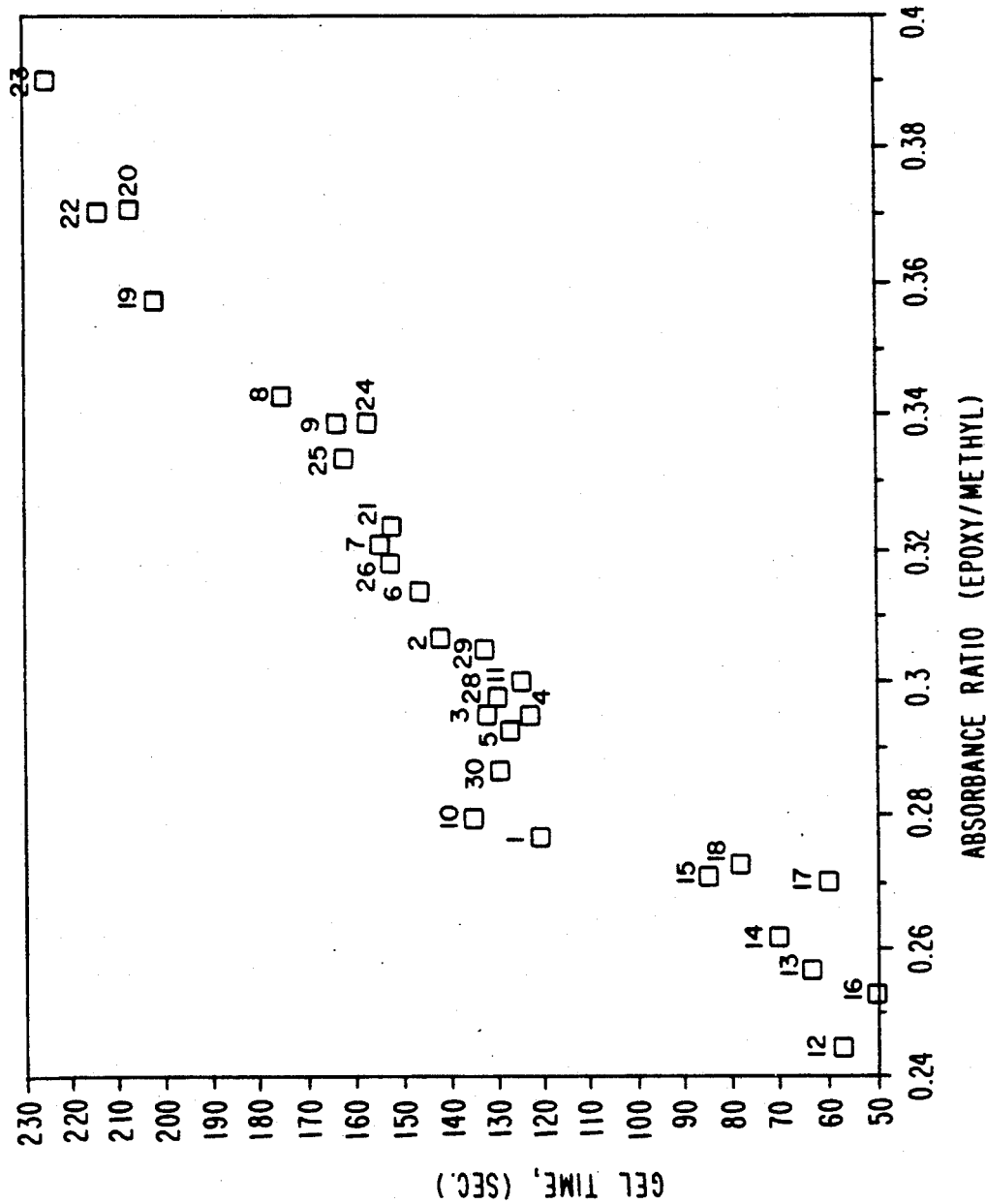
FIGS. 7 to 10 represent calibrations prepared as described in Example 2.
Figure 8:
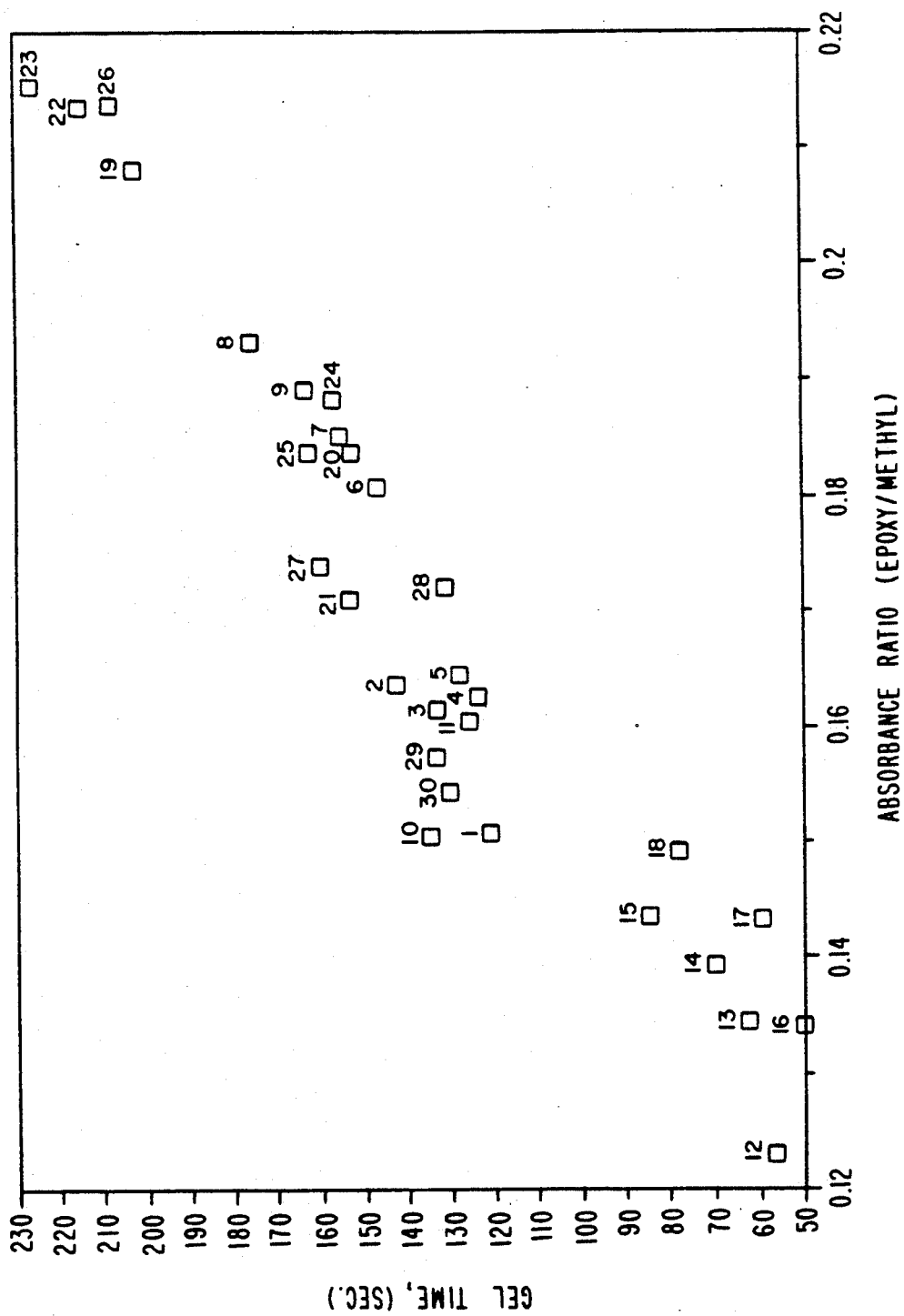
Figure 9:
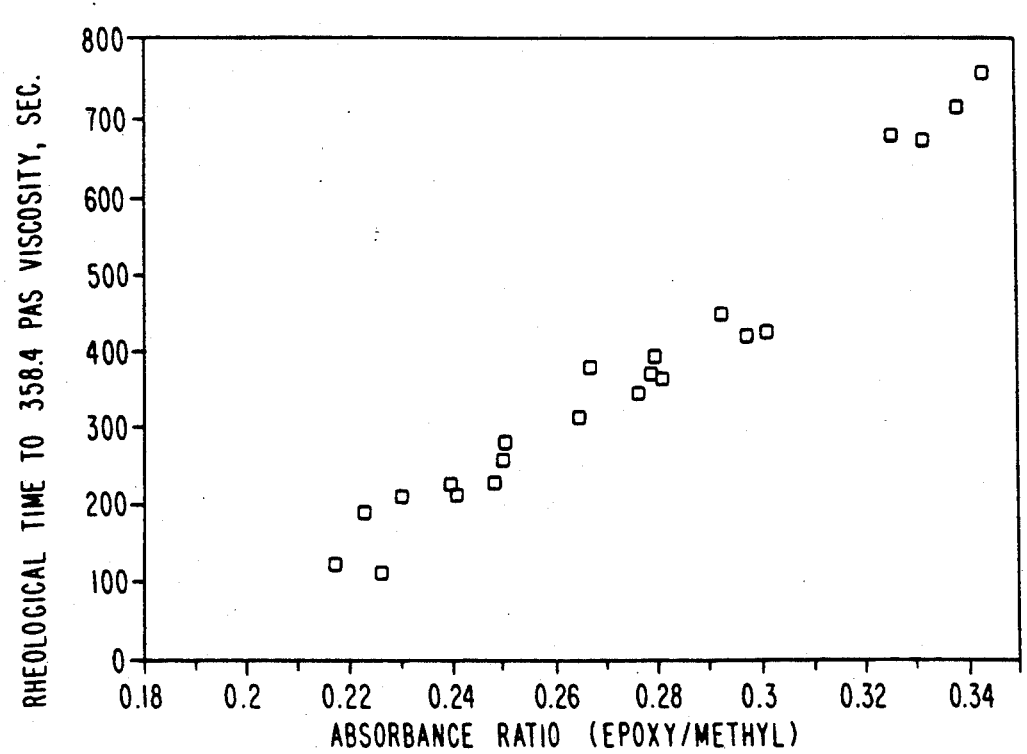
Figure 10:
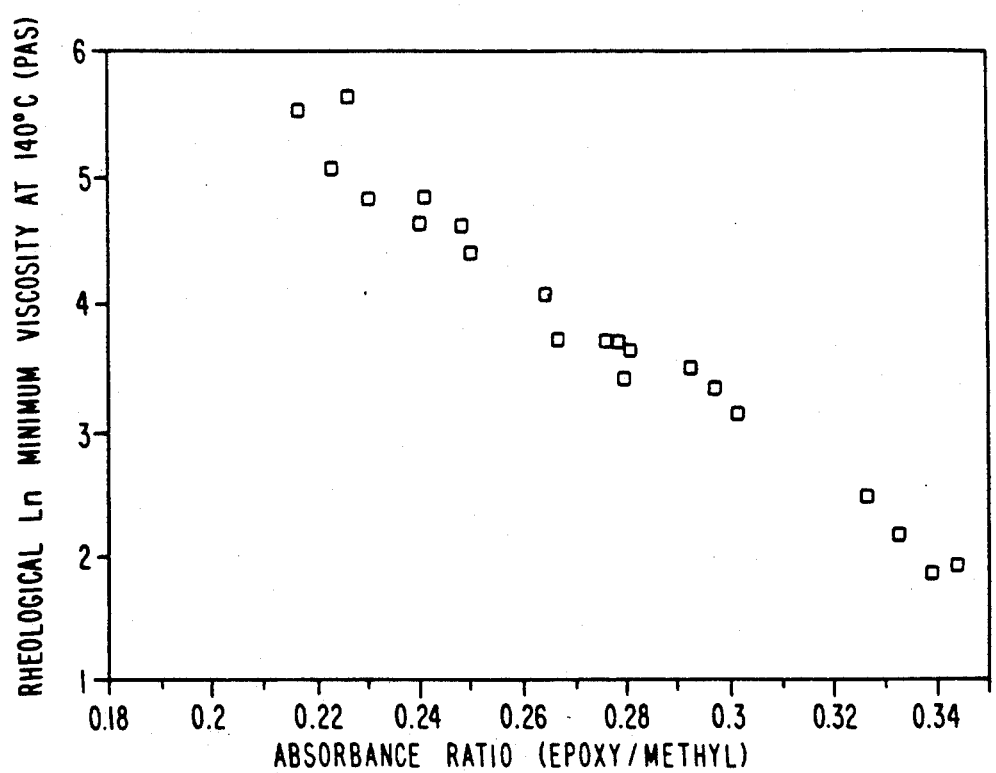

In this manner the method according to the present invention was repeated for various prepregged samples using the three commercial spectrometer devices noted above. The prepreg samples were also subjected to testing using the IPC gel time Testing Method No. 2.3.18 and rheology testing. The results of these measurements are correlated and shown in FIGS. 7 to 10. More particularly, FIG. 7 illustrates the correlation the absorbance ratios calculated from the spectral analysis provided by the Biorad FTS-7 spectrometer with gel time measurements, while FIG. 8 shows the correlation of the absorbance ratios calculated from the spectral analysis provided by the Nicolet 8205 spectrometer with the gel time measurements. FIGS. 9 and 10 illustrate the correlation of the absorbance ratios calculated from the spectral analysis provided by the Analect FSS 40 spectrometer with the values resulting from the rheological testing. The data set forth in FIGS. 7 through 10 may be used for the measurement of the degree of cure of new samples of prepreg in order to quickly evaluate the degree of cure in terms of a known property such as gel time or minimum viscosity.

EXAMPLE 3

This example further demonstrates the methods according to the present invention. The composite material employed in this example was similar to that described in Example 1 except that a multifunctional epoxy was added to improve physical performance. The resin formulation comprised 84 parts by weight of the brominated epoxy resin described in Example 1, 2.6 to 2.9 parts by weight dicyandiamide curing agent, 0.03 to 0.05 parts 2-methylimdazole curing agent, 8 parts Dow Chemical XD-9053 multifunctional epoxy resin, 12 parts methylcelosolve, 9 parts DMF, and 36 parts acetone. The prepreg was prepared in a production treater in a manner common to the prepreg manufacturing industries. A set of samples with various degrees of cures was prepared by changing the temperature and/or duration time in the prepregging oven and obtaining samples from production batches.

Figure 11:
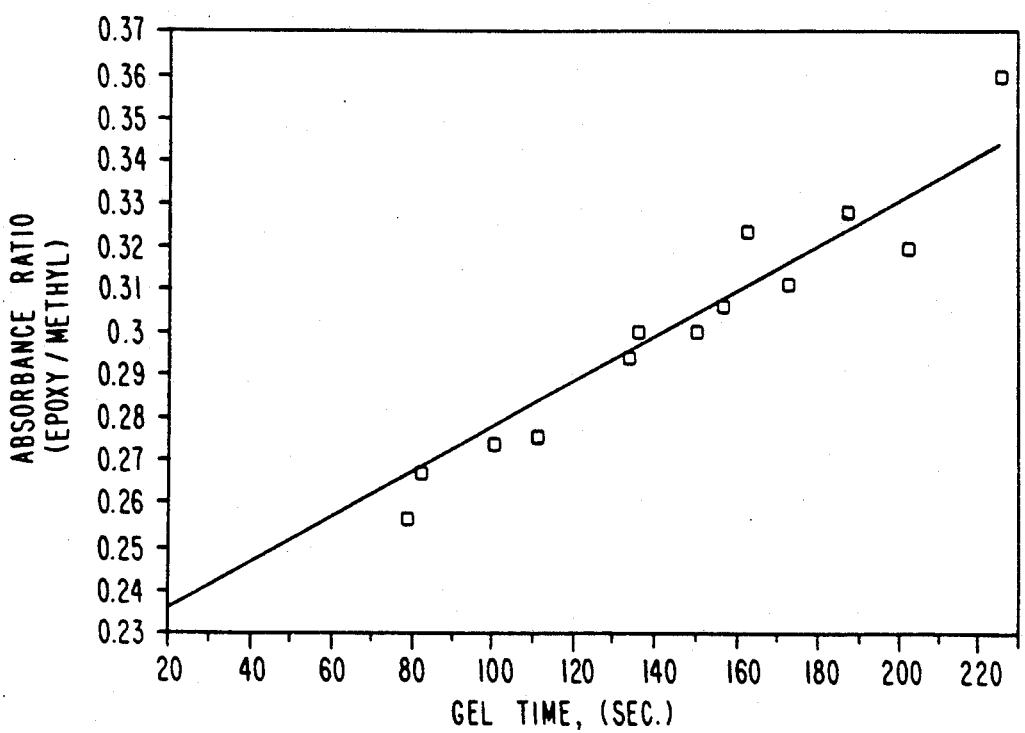
FIG. 11 represents the calibration prepared as described in Example 3.

Pieces of the prepreg were cut and subjected to measurement according to the present method using the IR absorbance frequencies described in Example 1 and the gel time tests described above. Again, a correlation between gel times and IR absorbance ratios was developed, as is illustrated in FIG. 11. This correlation is different than observed for the unmodified epoxy system but can still be used to quickly evaluate the degree of cure of subsequent prepreg samples prepared using similar multifunctional epoxy-modified resin systems.

EXAMPLE 4

This example further demonstrates the methods according to the present invention, with attention directed to the amount of resin included in a composite material. The composite material used in this example was similar to that described in Example 1. The samples were prepared in a production treater and came from a number of different production batches.

Each sample was cut to a specific size and weighed in order to determine the total mass of the sample. The mass of the resin was then determined by subtracting the mass of the glass from the total mass. The mass of the glass was calculated from standardized mass per unit area information available from the glass industry.

Figure 12:
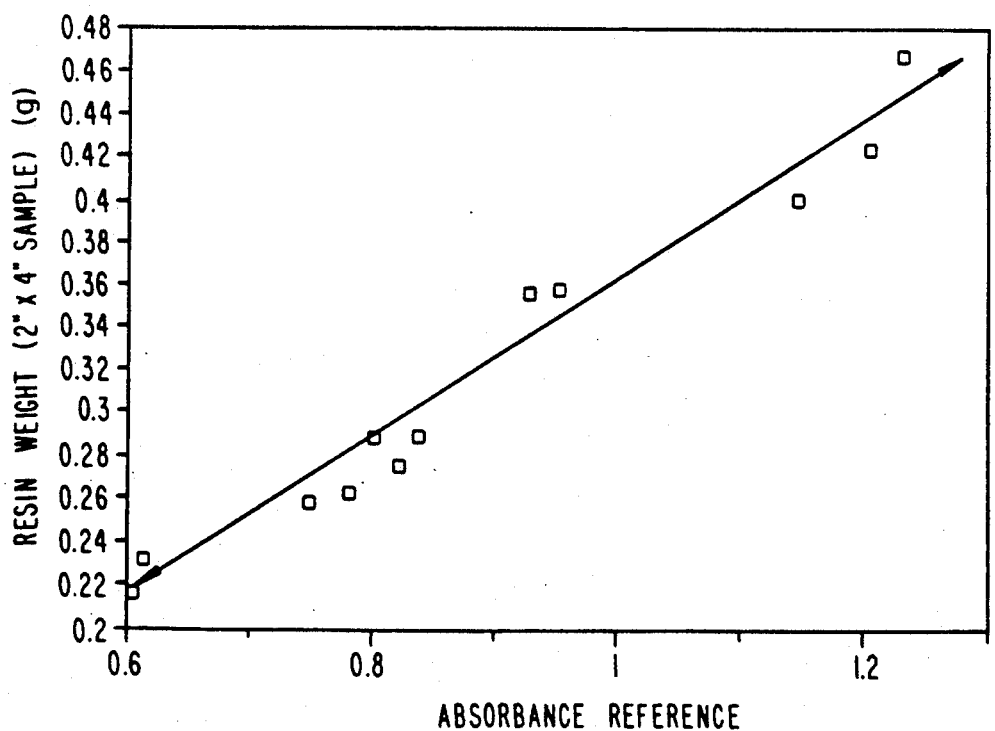
FIG. 12 represents the calibration prepared as described in Example 4.

The samples were then analyzed by IR absorbance in accordance with the present method. A correlation as is shown on FIG. 12 was derived relating the total resin mass to the IR reference value. This correlation has provided a quick, simple method of determining the resin content in this composite material.

EXAMPLE 5

This example again demonstrates the methods according to the present invention with regard to resin content; however, the composite material used in this example was bismaleimide resin commonly called "KERIMID 601" which is commercially available. The samples were prepared on a production treater and came from a number of different batches.

Figure 13:
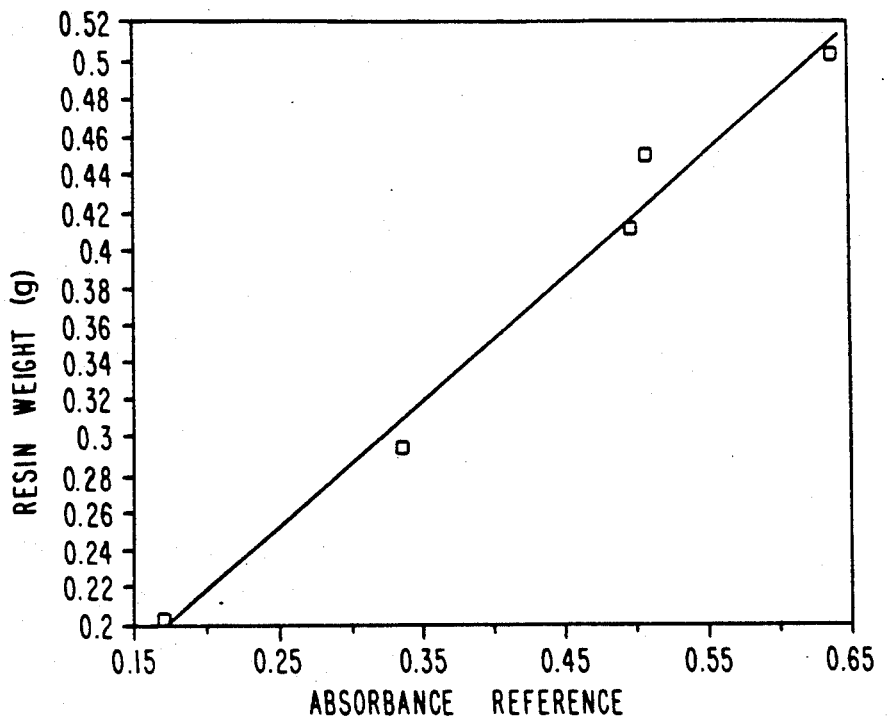
FIG. 13 represents the calibration prepared as described in Example 5.

Each sample was cut to a specific size and the resin mass was determined as in Example 4. The samples were then analyzed by IR absorbance at a centered, nonreactive reference frequency of 4620 cm$^{-1}$ to determine a reference height and/or area representative of the total mass of the resin. FIG. 13 portrays a correlation derived between these two parameters and demonstrates the applicability of this resin content measurement technique to other resin systems.

EXAMPLE 6

This example further demonstrates the methods according to the present invention. The composite material employed in this example is similar to the material used in Example 5. The material came from a production batch and was prepared on a production treater. Different states of cure were obtained in the samples by curing in a lab oven for various amounts of time.

Samples were cut from a sheet of prepreg and subjected to the IR absorbance analysis at two different frequencies but still in accordance with the present method. The nonreactive reference frequency was that described in Example 5 and the reactive group frequency, a maleimide functional group, was centered at 3100 cm$^{-1}$.

Figure 14:
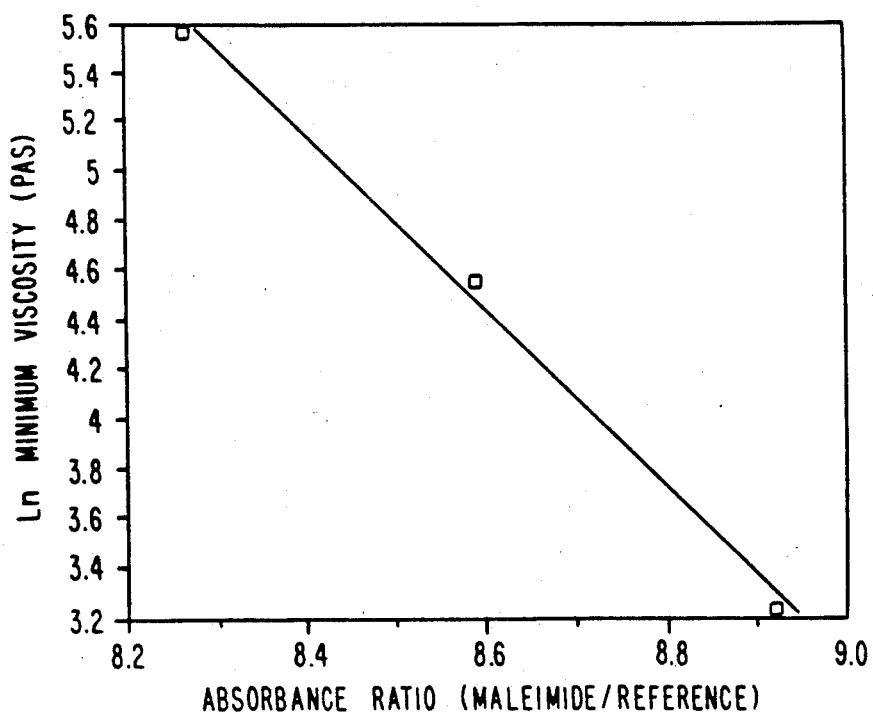
FIGS. 14 and 15 represent calibrations prepared as described in Example 6.
Figure 15:
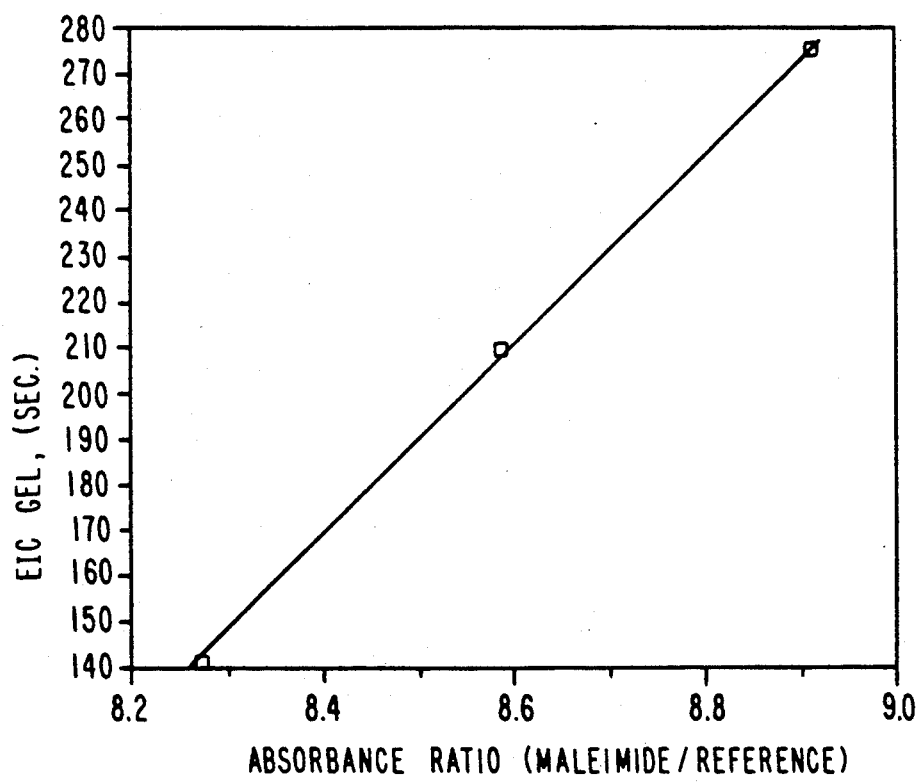

The resulting calculated ratios were then correlated with rheology testing and the results are shown in FIGS. 14 and 15. This correlation may be used to quickly evaluate the degree of cure of new prepreg samples prepared with KERIMID 601 resin, and demonstrates that this technique may also be used for composite materials of resin chemistry other than epoxy.

EXAMPLE 7

Figure 25:
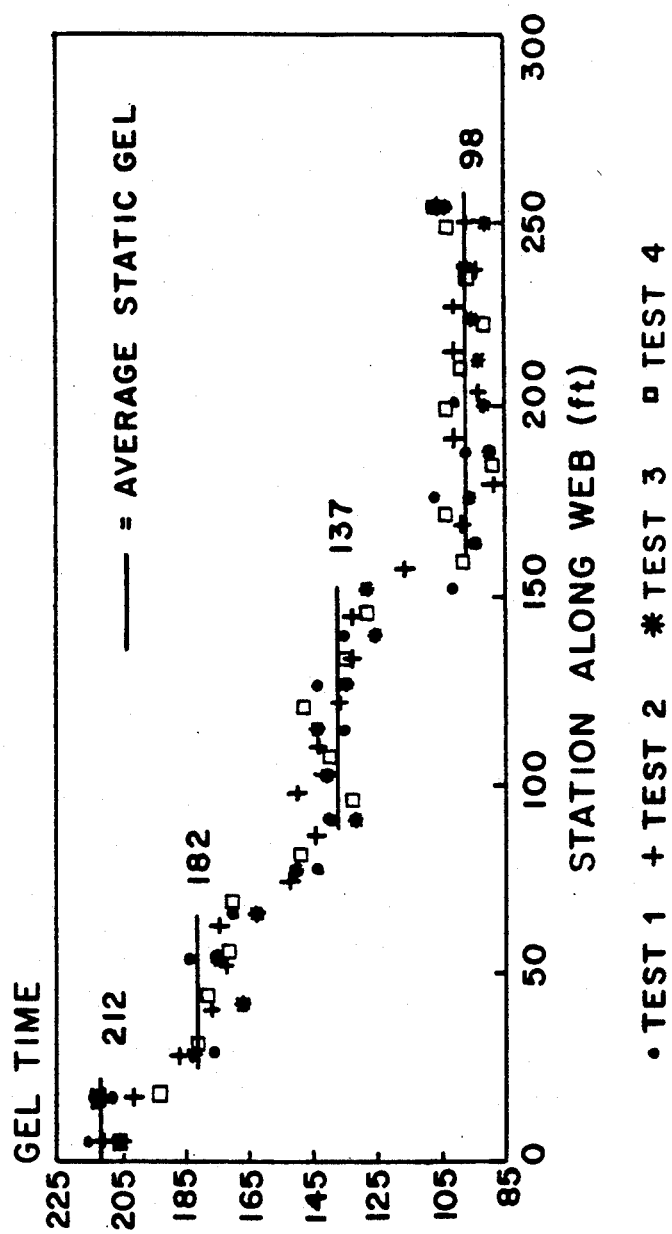
FIG. 25 is a graph illustrating the testing accuracy of the present invention in an on-line production process for producing prepregs.

FIG. 25 is a graph illustrating the testing accuracy and repeatability of the present invention in an on-line production process for producing prepregs.

To generate the data which is graphically shown on FIG. 25, a composite web was produced in a normal manner and an FTIR device having a configuration similar to that of the embodiment of FIG. 23 but held in a stationary position, and operating in accordance with the present invention's teachings was used to monitor the degree of cure of the resin in both a static mode of operation wherein a sample of the web was held stationary, and in the dynamic mode of operation of the web, wherein the web was moving at a rate of about 250 inches per minute. The speed of the moving web being produced was slowly decreased and periodically halted (causing the discontinuities or "steps" in the gel time being measured which would not normally be expected.) Four runs indicated as Test 1-4 were performed wherein the FTIR was used to sample a portion of the web each 30 seconds. The results of each of the dynamic samplings of each of Tests 1-4 and how they correlate with a static sample in each section are illustrated and it is readily apparent that excellent accuracy is achieved with use of the present invention. These results show that the method of the present invention provides excellent test sensitivity to changes in the degree of cure caused by the decreasing speed of the production web, excellent repeatability between successive measurements, as well as excellent repeatability between the different test runs, i.e. Tests 1-4.

While the preceding examples are set forth to illustrate specific embodiments of the invention, they are not intended to limit the scope of the invention, nor the scope of compositions or methods by which the present invention may be practiced. Additional embodiments and advantages which are circumscribed by the appendant claims are considered part of the invention and will be apparent to one of ordinary skill in the art.

What is claimed is:

1. A method for measuring a degree of cure of a resin in a composite material for the production of electronic circuit boards, comprising the steps of:

(a) irradiating the composite material with infrared light from an infrared light source of an infrared spectrometer device having means for resolving specific frequency absorbance information and means for providing a quantitative spectral analysis of the amount of energy absorbed at first and second frequencies of unreactive and cure-reactive groups, respectively, contained in the resin;

(b) irradiating the composite material being produced with infrared light from the infrared light source so to transmit at least a portion of the radiation through the said composite material and detecting the transmitted infrared light;

(c) generating a quantitative spectral analysis of the amount of energy absorbed at the first and second frequencies;

(d) determining the height of or area under the spectrum maximum of each of the first and second frequencies; and (e) calculating a ratio of one of the determined values to the other determined value to provide a measurement indicative of the degree of cure of the resin.

2. A method as defined by claim 1, wherein the infrared spectrometer device comprises a Fourier transform infrared spectrometer (FTIR).

3. A method as defined by claim 1, wherein the composite material comprises a reinforcement matrix or web which is coated or impregnated with the resin.

4. A method as defined by claim 3, wherein the reinforcement matrix or web comprises glass, quartz, graphite or an aromatic polyamide.

5. A method as defined by claim 1, wherein the resin comprises a thermoset polymer.

6. A method as defined by claim 1, wherein the resin comprises reactive groups selected from the group consisting of: methyl, epoxy, nitrile, maleimide groups.

7. A method as defined by claim 6, wherein the resin comprises an epoxy group as the reactive group.

8. A method as defined by claim 1, wherein the height of the spectrum maximum at each of the first and second frequencies is determined.

9. A method as defined by claim 8, wherein the ratio of the height of the spectrum maximum at the first frequency to the height of the spectrum maximum of the second frequency is calculated.

10. A method as defined by claim 8, wherein the ratio of the height of the spectrum maximum at the second frequency to the height of the spectrum maximum of the first frequency is calculated.

11. A method as defined by claim 1, wherein the area under the spectrum maximum at each of the first and second frequencies is determined.

12. A method as defined by claim 11, wherein the ratio of the area under the spectrum maximum at the first frequency to the area under the spectrum maximum at the second frequency is calculated.

13. A method as defined by claim 11, wherein the ratio of the area under the spectrum maximum at the second frequency to the area under the spectrum maximum at the first frequency is calculated.

14. A method as defined by claim 13, which includes the additional step of comparing the calculated ratio to a predetermined calibration between calculated ratios and measured gel times.

15. A method for producing a resin containing composite material for the production of electronic circuit boards in a conventional production apparatus which comprises the process steps of:

(a) providing an infrared light source and an infrared spectrometer device having means for resolving specific frequency absorbance information and means for providing a quantitative spectral analysis of the amount of energy absorbed at first and second frequencies associated with unreactive and cure reactive groups, respectively, contained within the resin of the composite material;

(b) irradiating the composite material with infrared light from the infrared light source so to transmit at least a portion of the radiation through the composite material and detecting said transmitted light, (c) operating the infrared spectrometer device to generate a quantitative spectral analysis of the amount of energy absorbed at first and second frequencies associated with said unreactive and cure reactive groups, (d) determining the height of or area under the spectrum maximum of each of the first and second frequencies, and (e) calculating a ratio of one of the determined values to the other determined value to provide a measurement of the degree of cure of the resin.

16. The method according to claim 15, which further includes the process step of:

generating a control signal which is dependent upon the measurement obtained in step (e), and using the control signal to control a process variable within the conventional production apparatus.

17. The method according to claim 16, which further comprises the process steps of:

providing in the conventional production apparatus a pair of metering rollers which limits the amount of resin which is impregnated within the composite material, and variably establishing as said process variable the intermediate distance between the roll centers of the metering rollers responsive to the control signal to limit the amount of resin which is impregnated within the composite material.

18. The method according to claim 16, which further comprises the process steps of:

providing in the conventional production apparatus a drying/curing oven, and, variably establishing as said process variable the mode of the operation of the drying/curing oven responsive to the control signal to limit the degree of cure of resin which is impregnated within the composite material.

19. The method according to claim 18, wherein the drying/curing oven has a plurality of heating zones.

20. The method according to claim 16, which includes the process steps of:

providing in the conventional production apparatus a drying/curing oven which comprises a plurality of heating zones, and, variably establishing as said process variable the mode of the operation of the individual heating zones of the drying/curing oven responsive to the control signal to limit the degree of cure of resin which is impregnated within the composite material.

21. The method according to claim 17, wherein the infrared spectrometer device comprises a single IR light source and a single IR light receiver.

22. The method according to claim 17, wherein the infrared spectrometer device comprises a plurality of IR light sources and a plurality of IR light receivers.

23. The method according to claim 22, wherein each of the plurality of IR light sources and plurality of corresponding IR light receivers individually impinges only on a portion of the composite material.

24. The method according to claim 23, wherein each of the plurality of IR light sources and plurality of corresponding IR light receivers individually impinging on only a portion of the composite material are used to determine the degree of cure of the resin of the portion of the composite material upon which they impinge.

25. An apparatus for the production of electronic circuit boards which comprises:
- a vessel containing a quantity of resin used to impregnate the web,
- an infrared spectrometer device having an infrared light source, means for resolving specific frequency absorbance information and means for providing a quantitative spectral analysis of the amount of energy absorbed at first and second frequencies of unreactive and cure-reactive groups, respectively, contained in the resin, means for irradiating the composite material being produced with infrared light from the infrared light source so as to transmit at least a portion of the radiation through the said composite material and detecting the transmitted infrared light, means for generating a quantitative spectral analysis of the amount of energy absorbed at the first and second frequencies, means for determining the height of or area under the spectrum maximum of each of the first and second frequencies, and means for calculating a ratio of one of the determined values to the other determined value to provide a measurement indicative of the degree of cure of the resin,
- means for generating a control signal responsive to the means for calculating a ratio of one of the determined values to the other determined value to provide a measurement indicative of the degree of cure of the resin,
- and a drying/curing oven operative in response to said control signal to limit the degree of cure of resin which is impregnated within the composite material.

26. The apparatus according to claim 25 which further comprises a pair of metering rollers operative in response to said control signal to limit the amount of resin impregnated in said composite material.

* * * * *